US011383031B2

(12) United States Patent
Tominaga et al.

(10) Patent No.: US 11,383,031 B2
(45) Date of Patent: Jul. 12, 2022

(54) CATHETER ASSEMBLY

(71) Applicant: TERUMO KABUSHIKI KAISHA, Tokyo (JP)

(72) Inventors: Takanori Tominaga, Hadano (JP); Shinya Kusunoki, Hakui (JP); Ryoji Kobayashi, Hadano (JP); Tadasu Tateishi, Hadano (JP); Masahiro Ishida, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 258 days.

(21) Appl. No.: 16/560,406

(22) Filed: Sep. 4, 2019

(65) Prior Publication Data
US 2019/0388616 A1 Dec. 26, 2019

Related U.S. Application Data

(63) Continuation of application No. PCT/JP2018/011363, filed on Mar. 22, 2018.

(30) Foreign Application Priority Data

Mar. 22, 2017 (JP) .............................. JP2017-055228

(51) Int. Cl.
*A61M 5/158* (2006.01)
*A61M 25/06* (2006.01)
(Continued)

(52) U.S. Cl.
CPC .......... *A61M 5/158* (2013.01); *A61M 5/3287* (2013.01); *A61M 5/3293* (2013.01);
(Continued)

(58) Field of Classification Search
CPC .......... A61M 25/0606; A61M 25/0612; A61M 25/0618; A61M 25/0625; A61M 25/0631;
(Continued)

(56) References Cited

U.S. PATENT DOCUMENTS

| 2013/0023826 A1* | 1/2013 | Ishida | ................. A61M 5/158 |
| | | | 604/165.02 |
| 2015/0080801 A1* | 3/2015 | Tanabe | ............. A61M 25/0606 |
| | | | 604/167.02 |
| 2018/0099101 A1* | 4/2018 | Sealfon | ............... A61M 5/3245 |

FOREIGN PATENT DOCUMENTS

JP  2008-043445 A  2/2008
WO  WO-95/11710 A1  5/1995
(Continued)

OTHER PUBLICATIONS

International Search Report and Written Opinion dated Jun. 19, 2018 in International Patent Application No. PCT/JP2018/011363.
(Continued)

*Primary Examiner* — Laura A Bouchelle
(74) *Attorney, Agent, or Firm* — Foley & Lardner LLP

(57) ABSTRACT

A catheter assembly includes: a catheter; a catheter hub; an inner needle; a needle hub; and a deflection suppressing mechanism suppressing deflection of the inner needle. The deflection suppressing mechanism includes an upper deflection suppressing portion positioned on an upper side of the inner needle and a lower deflection suppressing portion positioned on a lower side of the inner needle. At least one of the upper deflection suppressing portion and the lower deflection suppressing portion is movable with respect to the needle hub.

11 Claims, 32 Drawing Sheets

(51) Int. Cl.
*A61M 5/32* (2006.01)
*A61M 25/09* (2006.01)

(52) U.S. Cl.
CPC ........ *A61M 25/0606* (2013.01); *A61M 25/09* (2013.01); *A61M 2005/1585* (2013.01)

(58) Field of Classification Search
CPC ................ A61M 5/158; A61M 5/3293; A61M 2005/1585
See application file for complete search history.

(56) References Cited

FOREIGN PATENT DOCUMENTS

| WO | WO-2011/118643 | A1 | | 9/2011 | |
|---|---|---|---|---|---|
| WO | WO-2015/115315 | A1 | | 8/2015 | |
| WO | WO-2015/115316 | A1 | | 8/2015 | |
| WO | WO-2015115315 | A1 | * | 8/2015 | ........ A61M 25/0631 |
| WO | WO-2016/185950 | A1 | | 11/2016 | |

OTHER PUBLICATIONS

International Searching Authority, "International Search Report," issued in connection with International Patent Application No. PCT/JP2018/011363, dated Jun. 19, 2018.

International Searching Authority, "Written Opinion," issued in connection with International Patent Application No. PCT/JP2018/011363, dated Jun. 19, 2018.

Office Action dated Aug. 17, 2021 issued in a corresponding Japanese Patent Application No. 2019-506965, (6 pages).

* cited by examiner

CATHETER ASSEMBLY

CROSS-REFERENCE TO RELATED APPLICATIONS

This is a bypass continuation of PCT Application No. PCT/JP2018/011363, filed on Mar. 22, 2018, which claims priority to Japanese Application No. 2017-055228, filed on Mar. 22, 2017. The contents of these applications are hereby incorporated by reference in their entireties.

BACKGROUND

The present disclosure relates to a catheter assembly configured to be punctured and remain indwelled in a blood vessel when performing an infusion or the like to a patient, for example.

Conventionally, a catheter assembly used when performing an infusion or the like to a patient has been known. This kind of the catheter assembly includes a hollow catheter, a catheter hub fixed to a proximal end of the catheter, a hollow inner needle that is inserted into the catheter and has a sharp needle tip at a distal end, and a needle hub fixed to a proximal end of the inner needle (for example, see JP 2008-43445 A). When using a catheter assembly, a skin and a blood vessel of a living body are punctured with each distal end of the inner needle and the catheter, and then, the catheter is advanced with respect to the inner needle so that the catheter is inserted into the blood vessel by a predetermined length.

SUMMARY

Meanwhile, such a catheter assembly has a problem that it is difficult to perform a puncturing operation because the inner needle is deflected during the puncturing operation. In addition, there is a problem that it is difficult for the catheter to advance into the blood vessel or the inner needle pierces the catheter when an operation of advancing the catheter once and then retracting the catheter has been performed. In particular, when the catheter assembly is configured as a central venous catheter, a PICC, a mid-line catheter, a long peripheral venous catheter, or the like, a length of the inner needle is set to be relatively long. Thus, the problem of the deflection of the inner needle becomes more remarkable.

Certain embodiments described in the present application have been developed in consideration of such problems, and one object of certain embodiments is to provide a catheter assembly capable of suppressing a deflection of an inner needle during use.

According to one embodiment, a catheter assembly includes: a catheter; a catheter hub provided on a proximal side of the catheter; an inner needle inserted through the catheter; a needle hub supporting a proximal portion of the inner needle; and a deflection suppressing mechanism that is provided on the needle hub and supports the inner needle via the catheter on a distal side of the catheter hub to suppress a deflection of the inner needle. The deflection suppressing mechanism has an upper deflection suppressing portion positioned on an upper side of the inner needle and a lower deflection suppressing portion positioned on a lower side of the inner needle. At least one of the upper deflection suppressing portion and the lower deflection suppressing portion is movable with respect to the needle hub in order to allow the catheter hub to be separated from the needle hub along with advancement of the catheter with respect to the inner needle.

According to the catheter assembly having the above configuration, it is possible to smoothly perform the puncturing operation because the deflection suppressing mechanism suppresses the deflection of the inner needle during a puncturing operation, and it is possible to perform an advancement operation of the catheter because the deflection suppressing mechanism does not inhibit movement of the catheter hub during the advancement operation of the catheter. In addition, the catheter can be advanced smoothly into the blood vessel. Further, it is possible to reduce piercing of the catheter caused by the inner needle when an operation of advancing the catheter once and then retracting the catheter has been performed.

The needle hub may include: a needle hub proximal portion arranged on the proximal side of the catheter hub; an upper extension portion that extends in a distal direction from the needle hub proximal portion and is positioned on the upper side of the inner needle; and a lower extension portion that extends in the distal direction from the needle hub proximal portion and is positioned on the lower side of the inner needle. The deflection suppressing mechanism may include: a first deflection suppressing member that has the upper deflection suppressing portion and is movably supported by the upper extension portion; and a second deflection suppressing member that has the lower deflection suppressing portion and is movably supported by the lower extension portion.

With the above configuration, the first deflection suppressing member and the second deflection suppressing member are individually movable with respect to the needle hub, and thus, the catheter hub can be passed smoothly.

The above catheter assembly may include: a guide wire inserted into the inner needle; and a guide wire operation member that is movable with respect to the needle hub and moves the guide wire with respect to the inner needle. The first deflection suppressing member and the second deflection suppressing member may be restricted by the guide wire operation member from being moved in a state where the guide wire operation member is positioned at an initial position, and the restriction by the guide wire operation member may be released when the guide wire operation member is moved to move the guide wire from an initial position to an advanced position.

With the above configuration, it is possible to prevent the movement restriction of the first deflection suppressing member and the second deflection suppressing member from being released before puncture of the catheter assembly.

The second deflection suppressing member may be restricted from moving downward by abutting on the first deflection suppressing member in a state where the restriction on the first deflection suppressing member and the second deflection suppressing member by the guide wire operation member is released before the catheter hub abuts on the first deflection suppressing member and the second deflection suppressing member.

With the above configuration, the second deflection suppressing member is prevented from rotating downward by its own weight before the catheter hub abuts on the second deflection suppressing member. As a result, it is possible to maintain a function of supporting the inner needle from the lower side even after the advancement operation of the guide wire and to favorably suppress the downward deflection of the inner needle.

The second deflection suppressing member may be restricted from moving downward by fitting to the first deflection suppressing member in a state where the restriction on the first deflection suppressing member and the second deflection suppressing member by the guide wire operation member is released before the catheter hub abuts on the first deflection suppressing member and the second deflection suppressing member.

With the above configuration, the second deflection suppressing member is prevented from rotating downward by its own weight before the catheter hub abuts on the second deflection suppressing member. As a result, it is possible to maintain a function of supporting the inner needle from the lower side even after the advancement operation of the guide wire and to favorably suppress the downward deflection of the inner needle.

The deflection suppressing mechanism may include a deflection suppressing member that integrally has the upper deflection suppressing portion and the lower deflection suppressing portion and is movably supported by the needle hub.

With the above configuration, it is possible to reduce the number of parts constituting the deflection suppressing mechanism and to simplify a structure.

The needle hub may include: a needle hub proximal portion arranged on the proximal side of the catheter hub; an upper extension portion that extends in a distal direction from the needle hub proximal portion and is positioned on the upper side of the inner needle; and a lower extension portion that extends in the distal direction from the needle hub proximal portion and is positioned on the lower side of the inner needle. The deflection suppressing member may be configured to be expandable in the lateral direction and be supported by one of the upper extension portion and the lower extension portion to be rotatable in the vertical direction such that expansion is restricted by an expansion restriction portion provided on the other of the upper extension portion and the lower extension portion. The deflection suppressing member may rotate along with advancement of the catheter hub. The restriction on the expansion by the expansion restriction portion may be released along with the rotation of the deflection suppressing member.

With the above configuration, when the catheter hub is moved in the distal direction in order to insert the catheter into the blood vessel, the catheter hub can be smoothly passed in the distal direction through the deflection suppressing mechanism.

The needle hub may include: a needle hub proximal portion arranged on the proximal side of the catheter hub; an upper extension portion that extends in a distal direction from the needle hub proximal portion and is positioned on the upper side of the inner needle; and a lower extension portion that extends in the distal direction from the needle hub proximal portion and is positioned on the lower side of the inner needle. The deflection suppressing member may be configured to be expandable in the lateral direction and be supported by at least one of the upper extension portion and the lower extension portion to be slidable in the distal direction such that expansion is restricted by an expansion restriction portion provided on the upper extension portion or the lower extension portion. The deflection suppressing member may move in the distal direction along with advancement of the catheter hub. The restriction on the expansion by the expansion restriction portion may be released along with the movement of the deflection suppressing member in the distal direction.

With the above configuration, when the catheter hub is moved in the distal direction in order to insert the catheter into the blood vessel, the catheter hub can be smoothly passed in the distal direction through the deflection suppressing mechanism.

The deflection suppressing member may be allowed to rotate toward the upper side or lower side along with the movement in the distal direction.

According to the above configuration, it is possible to reliably prevent the rotation of the deflection suppressing member until the deflection suppressing member advances.

The deflection suppressing member may include first and second support members rotatably supported by one of the upper extension portion and the lower extension portion, and the first and second support members may be allowed to rotate in opposite directions to be expanded along with the movement in the distal direction.

With the above configuration, it is possible to effectively suppress the deflection of the inner needle because the inner needle is supported by the first and second support members, and to reliably prevent the expansion of the deflection suppressing member until the deflection suppressing member advances.

The deflection suppressing member may move in the distal direction to be separated from the needle hub along with the advancement of the catheter hub.

As a result, a mechanism that separates the catheter hub from the needle hub along with the advancement of the catheter hub can be realized with a simple configuration.

The deflection suppressing member may be held by the catheter hub along with the advancement of the catheter hub.

With the above configuration, the deflection suppressing member is not separated from other members alone along with withdrawal of the inner needle from the catheter, and thus, handling in a medical field is excellent.

One of the upper deflection suppressing portion and the lower deflection suppressing portion may be provided on a deflection suppressing member rotatably supported by the needle hub, and the other of the upper deflection suppressing portion and the lower deflection suppressing portion may be a protrusion provided on the needle hub.

As a result, the deflection suppressing mechanism can be realized with a simple configuration.

The protrusion may be an elastic piece that is elastically deformable in a direction away from the inner needle.

With this configuration, the catheter hub can be passed without deflecting the inner needle.

According to certain embodiments described in the present disclosure, it is possible to suppress the deflection of the inner needle during use.

The deflection suppressing mechanism may include: a first deflection suppressing member that has the upper deflection suppressing portion and is movably supported by the needle hub; and a second deflection suppressing member that has the lower deflection suppressing portion and holds the catheter hub in a detachable manner in an initial state.

With this configuration, the second deflection suppressing member can be gripped to advance the catheter, and thus, it is possible to improve the operability in the advancement operation of the catheter.

In the first deflection suppressing member, the suppression of the deflection of the inner needle performed by the upper deflection suppressing portion may be released along with advancement of the second deflection suppressing member.

With this configuration, the suppression of the deflection of the inner needle performed by the upper deflection suppressing portion can be released without directly operating the first deflection suppressing member, and thus, it is possible to improve the operability.

The second deflection suppressing member may be separable into a plurality of members.

With this configuration, it is possible to suppress kinking of the catheter at the time of detaching the second deflection suppressing member from the catheter hub.

The second deflection suppressing member may include a flexible portion extending around the catheter.

With this configuration, it is possible to suppress the deflection of the inner needle using the flexible portion, and the flexible portion is bent at the time of advancing the catheter so as not to prevent the advancement of the catheter.

DETAILED DESCRIPTION

Figure 1:
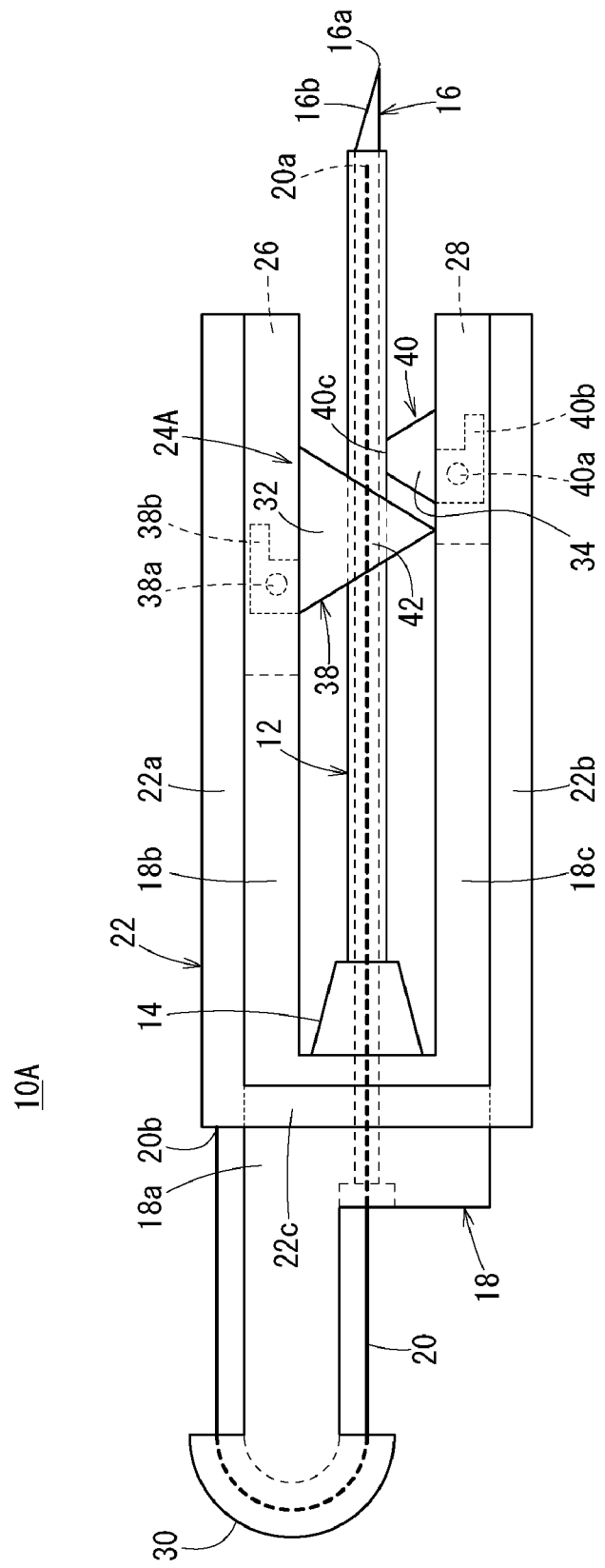
FIG. 1 is a schematic side view of a catheter assembly according to a first embodiment of the present invention.

Hereinafter, a plurality of embodiments of a catheter assembly according to the present invention will be described with reference to the accompanying drawings. Incidentally, the same or similar elements in second to tenth embodiments as those of a first embodiment will be denoted by the same reference numerals, and a detailed description thereof will be omitted. The same or similar functions and effects as those of the first embodiment can be obtained in the second to tenth embodiments for common parts with the first embodiment.

First Embodiment

A catheter assembly 10A according to a first embodiment illustrating an initial state in FIG. 1 is applied when performing an infusion, a blood transfusion, and the like to a patient (living body), and constructs an introduction portion of a medicinal liquid or the like by being punctured into the patient's body to remain indwelled. The catheter assembly 10A may be configured as a catheter (for example, a central venous catheter, a PICC, a mid-line catheter, and the like) having a longer length than a peripheral venous catheter. Incidentally, the catheter assembly 10A may be configured as the peripheral venous catheter. In addition, the catheter assembly 10A is not limited to the venous catheter, and may be configured as an arterial catheter such as a peripheral arterial catheter.

As illustrated in FIG. 1, the catheter assembly 10A includes: a catheter 12; a catheter hub 14 provided at a proximal portion of the catheter 12; a hollow inner needle 16 inserted into the catheter 12; a needle hub 18 fixed to a proximal portion of the inner needle 16; a guide wire 20 inserted into the inner needle 16; a guide wire operation member 22 moving the guide wire 20; and a deflection suppressing mechanism 24A suppressing a deflection of the inner needle 16. Hereinafter, a direction along an axis of the inner needle 16 (a longitudinal direction of the catheter assembly 10A) will be referred to as an "axial direction" in some cases.

The catheter assembly 10A forms a multi-pipe structure (multi-pipe portion) in which the catheter 12 and the inner needle 16 are sequentially stacked in an initial state before use.

The catheter 12 is a medical thin tube having flexibility, and is made of, for example, a resin material (PTFE, ETFE, PFA, PP, or the like). A lumen is formed in the catheter 12 to penetrate therethrough. The lumen is formed to have a diameter capable of housing the inner needle 16 and capable of causing a medicinal liquid, blood, or the like to flow.

A length of the catheter 12 is not particularly limited but can be appropriately designed according to use and various conditions, and is set to, for example, about 14 to 500 mm, about 30 to 400 mm, or about 76 to 200 mm.

A distal portion of the catheter hub 14 is fixed to the proximal portion of the catheter 12. The catheter hub 14 is exposed on the patient's skin in a state where the catheter 12 has been inserted into a blood vessel, and indwelled together with the catheter 12 by being pasted with a tape or the like.

A hollow portion that communicates with the lumen of the catheter 12 and through that an infusion solution can flow is provided inside the catheter hub 14. A hemostatic valve, a plug, or the like (not illustrated) may be housed inside the hollow portion in order to prevent back-flow of blood at the time of puncture with the inner needle 16 and to allow infusion along with insertion of a connector of an infusion tube. The catheter hub 14 may be provided with a tab projecting outward, or a catheter operation member may be attached to the catheter hub 14, in order to easily operate the catheter hub 14.

A constituent material of the catheter hub 14 is not particularly limited, but a thermoplastic resin, such as polypropylene, polycarbonate, polyamide, polysulfone, polyarylate, and a methacrylate-butylene-styrene copolymer may be preferably applied.

The inner needle 16 is configured as a rigid hollow tube capable of puncturing the skin of a living body, and is arranged to penetrate through the lumen of the catheter 12 and the lumen of the catheter hub 14. The inner needle 16 is formed to have a total length longer than that of the catheter 12, and a sharp needle tip 16a is provided at a distal end thereof. A lumen penetrating in an axial direction of the inner needle 16 is provided inside the inner needle 16, and this lumen communicates with a distal opening 16b of the inner needle 16.

Examples of a constituent material of the inner needle 16 include a metal material such as stainless steel, aluminum or an aluminum alloy, and titanium or a titanium alloy, a hard resin, ceramics, and the like. Incidentally, the inner needle 16 may be a solid needle when the guide wire 20 is not provided.

The needle hub 18 holds the proximal portion of the inner needle 16. The needle hub 18 includes: a needle hub proximal portion 18a arranged on the proximal side of the catheter hub 14; an upper extension portion 18b that extends in a distal direction from the needle hub proximal portion 18a and is positioned on an upper side of the inner needle 16; and a lower extension portion 18c that extends in the distal direction from the needle hub proximal portion 18a and is positioned on a lower side of the inner needle 16.

The proximal portion of the inner needle 16 is fixed to the needle hub proximal portion 18a. The needle hub proximal portion 18a includes a lumen that communicates with the lumen of inner needle 16. The upper extension portion 18b and the lower extension portion 18c extend parallel to each other along the inner needle 16. Distal portions of the upper extension portion 18b and the lower extension portion 18c are positioned on the distal side of the inner needle 16 on the proximal side of the needle tip 16a. Therefore, the inner needle 16 projects in the distal direction from the distal portions of the upper extension portion 18b and the lower extension portion 18c.

Figure 2:
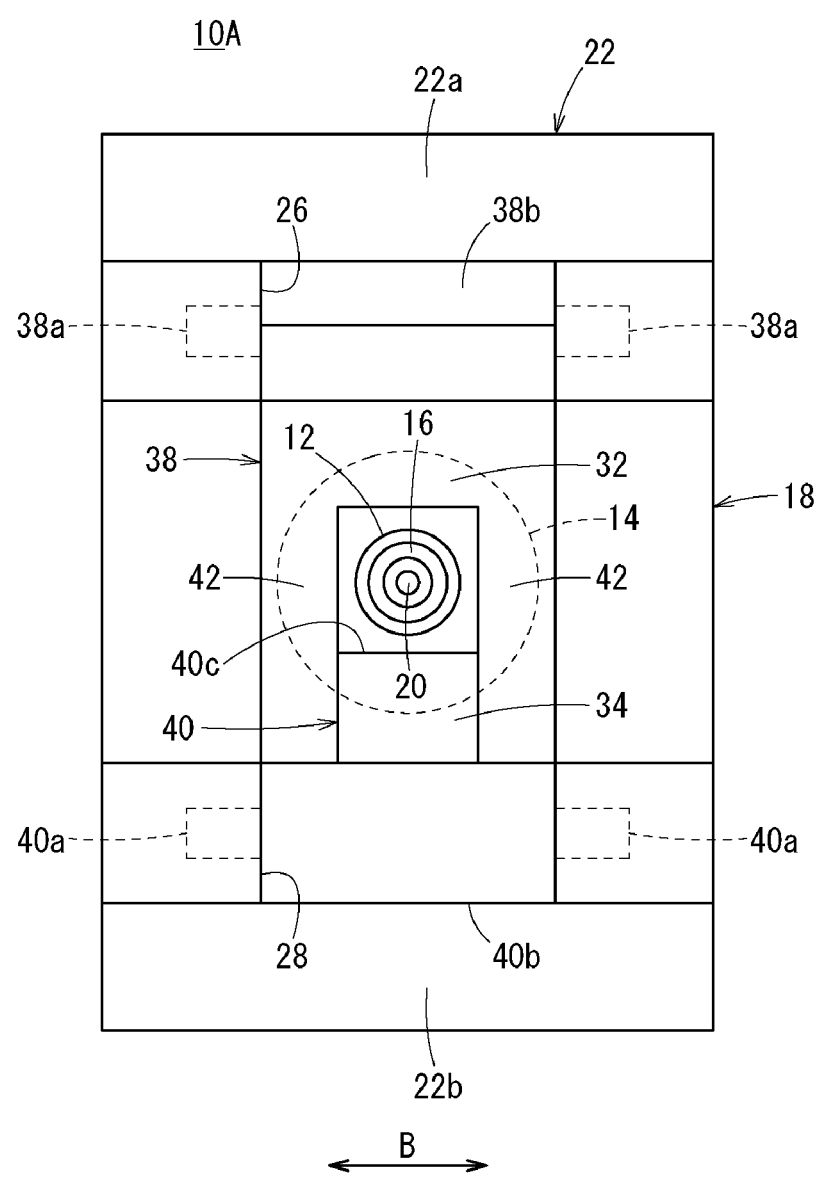
FIG. 2 is a front view of the catheter assembly illustrated in FIG. 1.

As illustrated in FIGS. 1 and 2, a first slit 26, which penetrates in a vertical direction and extends in a longitudinal direction of the upper extension portion 18b, is formed on the distal side of the upper extension portion 18b. A second slit 28, which penetrates in the vertical direction and extends in a longitudinal direction of the lower extension portion 18c, is formed on the distal side of the lower extension portion 18c. Lengths of the upper extension portion 18b and the lower extension portion 18c (positions of the distal portions of the upper extension portion 18b and the lower extension portion 18c) may be the same as or different from each other.

When the needle hub 18 is moved in a proximal direction with respect to the catheter 12, the inner needle 16 is also moved in the proximal direction with respect to the catheter 12 along with the movement of the needle hub 18 because the needle hub 18 holds the inner needle 16 as illustrated in FIG. 1. A resin material forming the needle hub 18 is not particularly limited, but, for example, the materials exemplified for the catheter hub 14 can be appropriately selected.

The guide wire 20 is a linear member having flexibility and is slidably inserted through the inside of the inner needle 16. A total length of the guide wire 20 is longer than a total length of the inner needle 16. In the initial state of the catheter assembly 10A, a distal end 20a that is one end of the guide wire 20 is positioned on the proximal side of the distal opening 16b of the inner needle 16. Another end 20b of the guide wire 20 is fixed to the guide wire operation member 22.

The guide wire 20 is slidably inserted through a guide wire guide portion 30 provided on the needle hub 18 on the proximal side of the inner needle 16. The guide wire 20 extending in the proximal direction from a proximal end of the needle hub 18 is folded back in the distal direction by the guide wire guide portion 30.

The guide wire operation member 22 is a member configured to move the guide wire 20 with respect to the inner needle 16, and is slidably supported by the needle hub 18 along the inner needle 16 (along a longitudinal direction of the needle hub 18). The guide wire operation member 22 includes: an upper arm 22a arranged on an upper surface of the upper extension portion 18b of the needle hub 18; a lower arm 22b arranged on a lower surface of the lower extension portion 18c; and a connection portion 22c that connects the upper arm 22a and the lower arm 22b. The guide wire 20 is folded back by the guide wire guide portion 30, and thus, moves in a direction opposite to a moving direction of the guide wire operation member 22 when the guide wire operation member 22 is moved.

The deflection suppressing mechanism 24A is provided on the distal side of the needle hub 18, and supports the inner needle 16 via the catheter 12 on the distal side of the catheter hub 14, thereby suppressing the deflection of the inner needle 16. The deflection suppressing mechanism 24A includes an upper deflection suppressing portion 32 positioned on the upper side of the inner needle 16 and a lower deflection suppressing portion 34 positioned on the lower side of the inner needle 16.

At least one of the upper deflection suppressing portion 32 and the lower deflection suppressing portion 34 is movable with respect to the needle hub 18 in order to allow the catheter hub 14 to move to the distal side of the deflection suppressing mechanism 24A along with advancement of the catheter 12 with respect to the inner needle 16. In the first embodiment, both the upper deflection suppressing portion 32 and the lower deflection suppressing portion 34 are movable with respect to the needle hub 18.

The upper deflection suppressing portion 32 and the lower deflection suppressing portion 34 are in proximity to or in contact with the catheter 12 between the initial state of the catheter assembly 10A and each vertical movement of the upper deflection suppressing portion 32 and the lower deflection suppressing portion 34.

Specifically, the deflection suppressing mechanism 24A includes: a first deflection suppressing member 38 that includes the upper deflection suppressing portion 32 and is movably supported by the upper extension portion 18b; and a second deflection suppressing member 40 that includes the lower deflection suppressing portion 34 and is movably supported by the lower extension portion 18c. The first deflection suppressing member 38 is rotatably supported by the upper extension portion 18b via a shaft 38a. The second deflection suppressing member 40 is rotatably supported by the lower extension portion 18c via a shaft 40a.

As illustrated in FIG. 2, the first deflection suppressing member 38 includes first and second lateral deflection suppressing portions 42 projecting downward from both ends of the upper deflection suppressing portion 32 in a width direction. In the initial state of the catheter assembly 10A, the pair of lateral deflection suppressing portions 42 is positioned on the left and right sides of the inner needle 16 and the catheter 12, and is in proximity to or in contact with the catheter 12. The first deflection suppressing member 38 and the second deflection suppressing member 40 suppress deflections of the catheter 12 in the vertical and lateral directions.

A first restricting abutment portion 38b is provided on an upper portion of the first deflection suppressing member 38. The first restricting abutment portion 38b is arranged in the first slit 26. In the initial state of the catheter assembly 10A, the first restricting abutment portion 38b abuts on a lower surface of the upper arm 22a of the guide wire operation member 22 so that the first deflection suppressing member 38 is prevented from rotating in a direction away from the catheter 12 (upward). When the guide wire operation member 22 moves in the proximal direction and a distal portion of the upper arm 22a moves to the proximal side of the first restricting abutment portion 38b, the restriction by the upper arm 22a is released, and the first deflection suppressing member 38 is allowed to rotate upward.

The second deflection suppressing member 40 is arranged on the distal side of the first deflection suppressing member 38. Incidentally, axial positions of the upper deflection suppressing portion 32 and the lower deflection suppressing portion 34 may partially overlap each other. In FIG. 2, a width (dimension along a direction of an arrow B) of a support face 40c of the second deflection suppressing member 40 (the lower deflection suppressing portion 34), which opposes the catheter 12, is preferably equal to or larger than an outer diameter of the catheter 12.

A second restricting abutment portion 40b is provided on a lower portion of the second deflection suppressing member 40. The second restricting abutment portion 40b is arranged in the second slit 28. In the initial state of the catheter assembly 10A, the second restricting abutment portion 40b abuts on an upper surface of the lower arm 22b of the guide wire operation member 22 so that the second deflection suppressing member 40 is prevented from rotating in a direction away from the catheter 12 (downward). When the guide wire operation member 22 moves in the proximal direction and a distal portion of the lower arm 22b moves to the proximal side of the second restricting abutment portion 40b, the restriction by the lower arm 22b is released, and the second deflection suppressing member 40 is allowed to rotate downward.

Next, functions of the catheter assembly 10A configured as described above will be described.

In use of the catheter assembly 10A illustrated in FIG. 1, a puncturing operation to puncture the patient's skin with the catheter assembly 10A is performed. In the puncturing operation, a user (a doctor, a nurse, or the like) presses the distal portion of the catheter assembly 10A against the patient while gripping the needle hub 18, thereby puncturing the skin toward a puncture target blood vessel. Accordingly, the skin is punctured with the inner needle 16 and each distal portion of the catheter 12.

Figure 3:
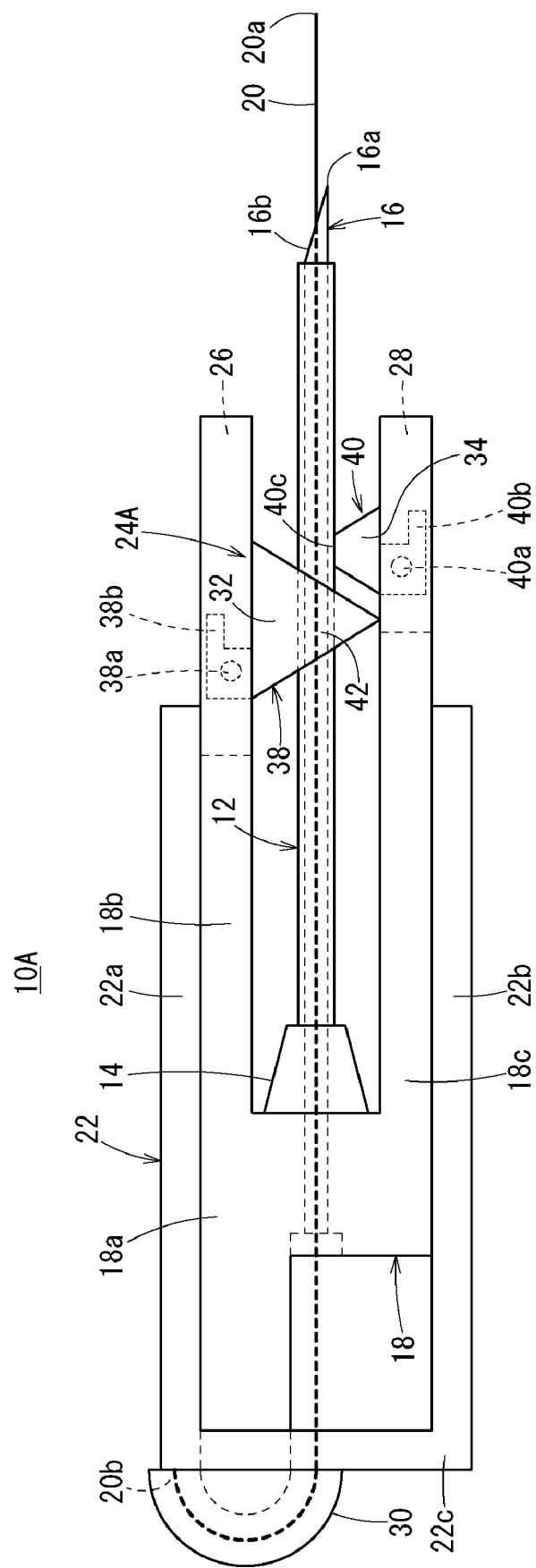
FIG. 3 is a first view for describing a function of the catheter assembly illustrated in FIG. 1.

After the puncture, the user moves the guide wire operation member 22 in the proximal direction with respect to the needle hub 18 to advance the guide wire 20 with respect to the inner needle 16 as illustrated in FIG. 3. As a result, the guide wire 20 projects from the distal opening 16b of the inner needle 16 by a predetermined length. When each distal portion of the upper arm 22a and the lower arm 22b of the guide wire operation member 22 moves to the proximal side of the first restricting abutment portion 38b and the second restricting abutment portion 40b as illustrated in FIG. 3, each of the first deflection suppressing member 38 and the second deflection suppressing member 40 is set to a state (lock release state) where the rotation in the vertical direction is allowed.

Figure 4:
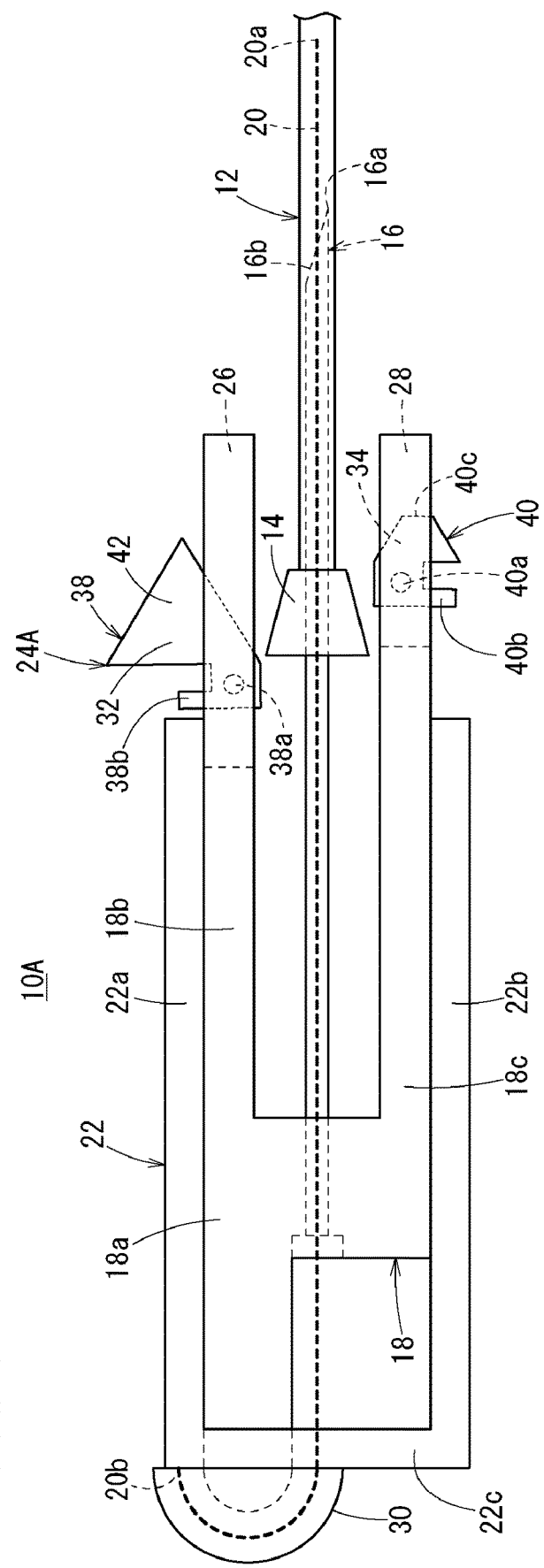
FIG. 4 is a second view for describing the function of the catheter assembly illustrated in FIG. 1.

Next, the user advances the catheter 12 while fixing the position of the needle hub 18 and gripping the catheter hub 14 (or the tab provided on the catheter hub 14 or the catheter operation member mounted on the catheter hub 14). Accordingly, the catheter 12 is inserted to the target position in the blood vessel. In the course of advancing the catheter 12, the first deflection suppressing member 38 and the second deflection suppressing member 40 rotate upward and downward, respectively, by being pushed by the catheter hub 14 as illustrated in FIG. 4. As a result, the catheter hub 14 can pass through the deflection suppressing mechanism 24A in the distal direction.

Next, the user pulls the needle hub 18 in the proximal direction while holding the position of the catheter 12. As a result, the inner needle 16 is withdrawn from the catheter 12 in the proximal direction. Then, the catheter 12 is caused to indwell in the patient.

Next, the connector of the infusion tube (not illustrated) is connected to the proximal side (the proximal portion of the catheter hub 14) of the catheter 12 from which the inner needle 16 has been removed, and the infusion solution (medicinal liquid) is administered from the infusion tube to the patient.

In this case, the catheter assembly 10A according to the present embodiment has the following effects.

The catheter assembly 10A includes the deflection suppressing mechanism 24A that supports the inner needle 16 via the catheter 12 on the distal side of the catheter hub 14 so as to suppress the deflection of the inner needle 16. The deflection suppressing mechanism 24A includes an upper deflection suppressing portion 32 positioned on the upper side of the inner needle 16 and a lower deflection suppressing portion 34 positioned on the lower side of the inner needle 16.

According to the catheter assembly 10A configured in this manner, the deflection of the inner needle 16 is suppressed by the deflection suppressing mechanism 24A at the time of the puncturing operation, and thus, it is possible to smoothly perform the puncturing operation. In addition, the catheter 12 can be smoothly advanced into the blood vessel. Further, it is possible to reduce piercing of the catheter 12 caused by the inner needle 16 when an operation of advancing the catheter 12 once and then retracting the catheter 12 has been performed.

At least one of the upper deflection suppressing portion 32 and the lower deflection suppressing portion 34 is movable with respect to the needle hub 18 in order to allow the catheter hub 14 to move to the distal side of the deflection suppressing mechanism 24A along with advancement of the catheter 12 with respect to the inner needle 16. As a result, the deflection suppressing mechanism 24A does not inhibit the movement of the catheter hub 14 during the advancement operation of the catheter 12, and thus, it is possible to perform the insertion of the catheter 12 into the blood vessel without any problem.

The deflection suppressing mechanism 24A includes: the first deflection suppressing member 38 that includes the upper deflection suppressing portion 32 and is movably supported by the upper extension portion 18b; and the second deflection suppressing member 40 that includes the lower deflection suppressing portion 34 and is movably supported by the lower extension portion 18c. With this configuration, the first deflection suppressing member 38 and the second deflection suppressing member 40 are individually movable with respect to the needle hub 18, and thus, the catheter hub 14 can be passed smoothly.

The first deflection suppressing member 38 and the second deflection suppressing member 40 are restricted from moving by the guide wire operation member 22 in the state where the guide wire operation member 22 is positioned at the initial position, and the restriction (lock) by the guide wire operation member 22 is released when the guide wire operation member 22 moves such that the guide wire 20 moves from an initial position to an advanced position. With this configuration, it is possible to prevent the movement restriction of the first deflection suppressing member 38 and the second deflection suppressing member 40 from being released before puncture of the catheter assembly 10A.

Second Embodiment

Figure 5:
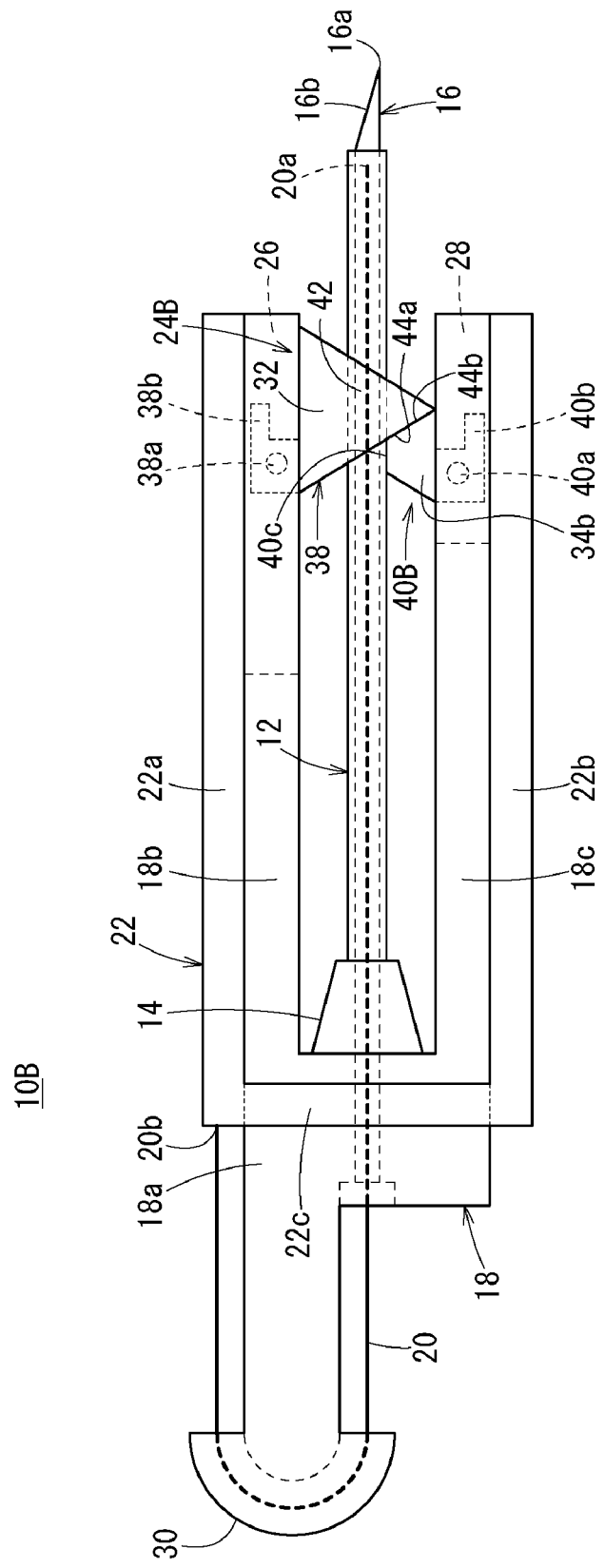
FIG. 5 is a schematic side view of a catheter assembly according to a second embodiment of the present invention.

A deflection suppressing mechanism 24B of a catheter assembly 10B according to a second embodiment illustrated in FIG. 5 includes the first deflection suppressing member 38 and a second deflection suppressing member 40B having a lower deflection suppressing portion 34b. The first deflection suppressing member 38 has the same configuration as the first deflection suppressing member 38 in the first embodiment, but is arranged on the distal side of the second deflection suppressing member 40B.

Figure 6:
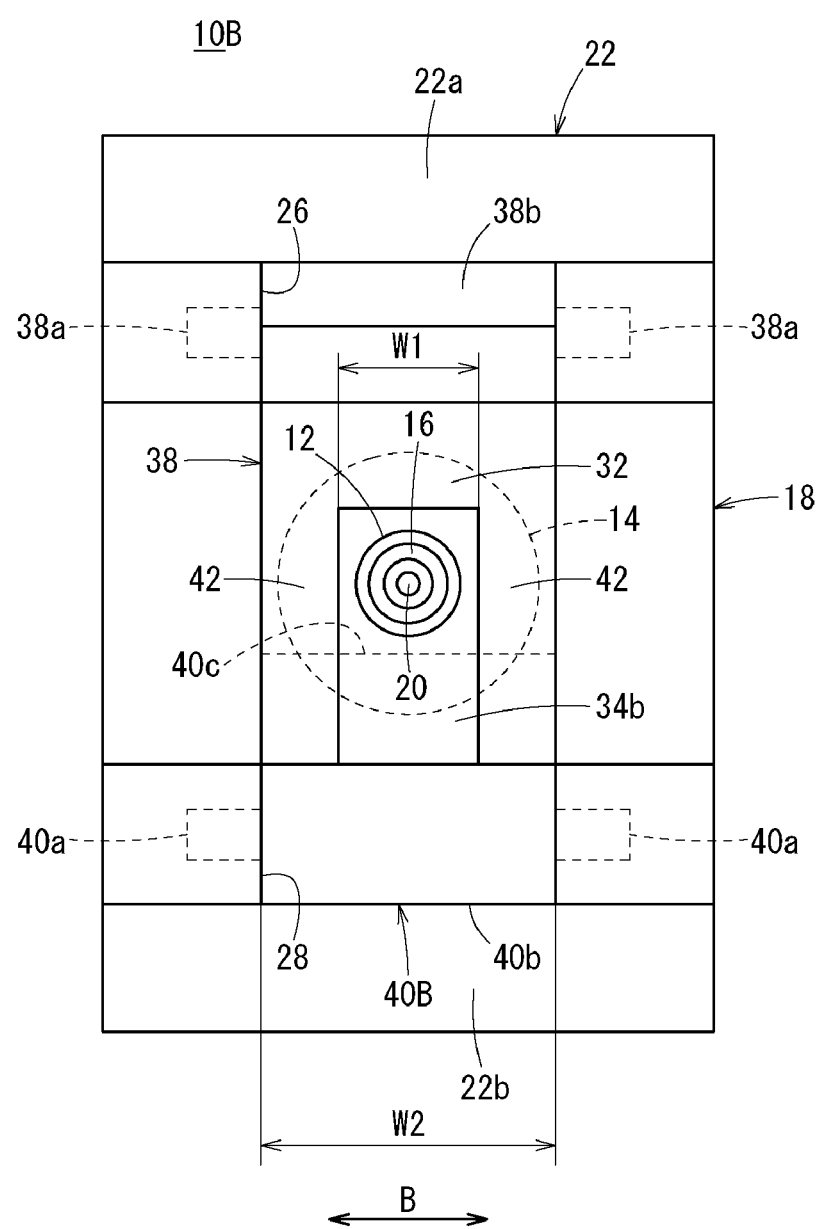
FIG. 6 is a front view of the catheter assembly illustrated in FIG. 5.

As illustrated in FIG. 6, a width W2 of the lower deflection suppressing portion 34b is larger than an interval W1 between the lateral deflection suppressing portions 42 (a width between inner surfaces of the lateral deflection suppressing portions 42). The width W2 of the lower deflection suppressing portion 34b may be equal to or larger than a width between outer surfaces of the lateral deflection suppressing portions 42.

As illustrated in FIG. 5, the first deflection suppressing member 38 has a proximal-side inclination surface 44a inclined with respect to the axis of the inner needle 16. The proximal-side inclination surface 44a is inclined to be away from the inner needle 16 in the distal direction. The proximal-side inclination surface 44a is formed in the lateral deflection suppressing portion 42. The second deflection suppressing member 40B has a distal-side inclination surface 44b inclined with respect to the axis of the inner needle 16. The distal-side inclination surface 44b is inclined to be away from the inner needle 16 in the distal direction. As illustrated in FIG. 5, the second deflection suppressing member 40B (the distal-side inclination surface 44b) abuts on the first deflection suppressing member 38 (the proximal-side inclination surface 44a) in an initial state of the catheter assembly 10B.

Figure 7:
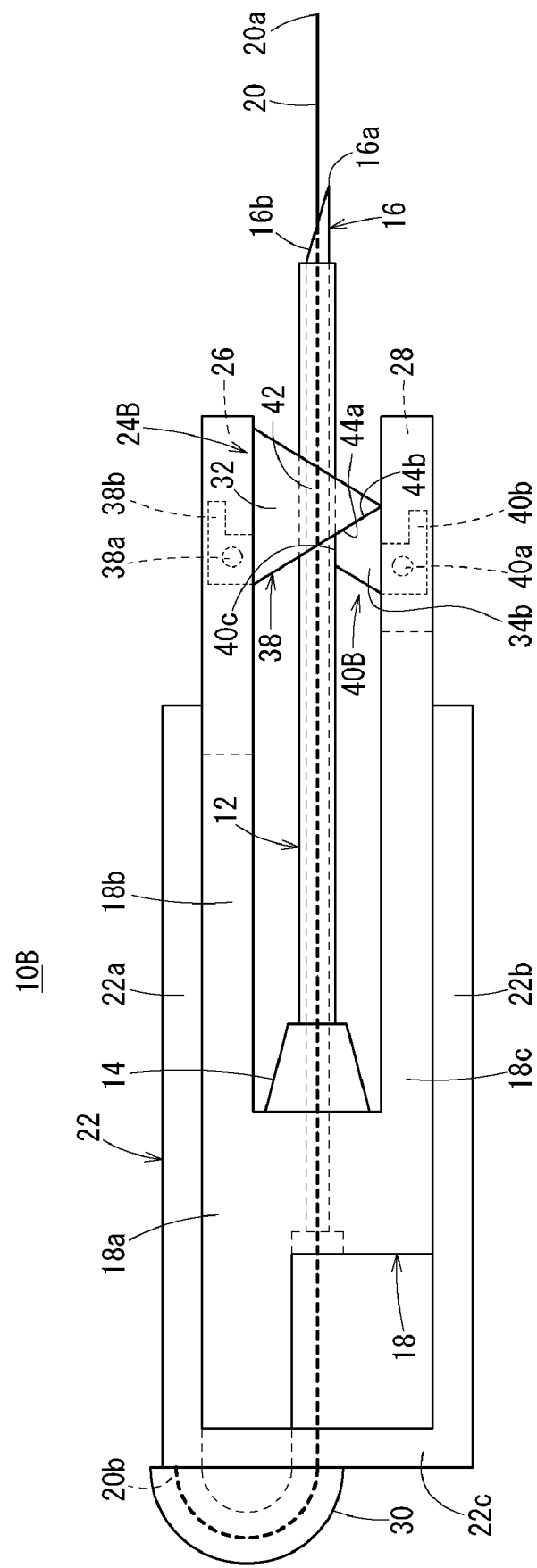
FIG. 7 is an explanatory view of a function of the catheter assembly illustrated in FIG. 5.

As illustrated in FIG. 7, the second deflection suppressing member 40B abuts on the first deflection suppressing member 38 to be restricted from moving downward in a state where restriction on the first deflection suppressing member 38 and the second deflection suppressing member 40B performed by the guide wire operation member 22 is released before the catheter hub 14 abuts on the first deflection suppressing member 38 and the second deflection suppressing member 40B.

According to the catheter assembly 10B, the deflection suppressing mechanism 24B suppresses deflections of the inner needle 16 in the vertical and lateral directions during a puncturing operation. Next, when the guide wire operation member 22 is moved in the proximal direction in order to advance the guide wire 20 as illustrated in FIG. 7, the restriction on the upward and downward rotations of the first deflection suppressing member 38 and the second deflection suppressing member 40B performed by the guide wire operation member 22 is released.

Then, when the catheter hub 14 is moved in the distal direction in order to insert the catheter 12 into the blood vessel, the first deflection suppressing member 38 and the second deflection suppressing member 40B are pushed in the distal direction by the catheter hub 14 so that the first deflection suppressing member 38 and the second deflection suppressing member 40B rotate upward and downward, respectively.

According to the catheter assembly 10B, the second deflection suppressing member 40B is prevented from rotating downward by its own weight before the catheter hub 14 abuts on the second deflection suppressing member 40B as illustrated in FIG. 7. As a result, it is possible to maintain a function of supporting the inner needle 16 from the lower side even after the advancement operation of the guide wire 20 and to favorably suppress the downward deflection of the inner needle 16.

Third Embodiment

Figure 8:
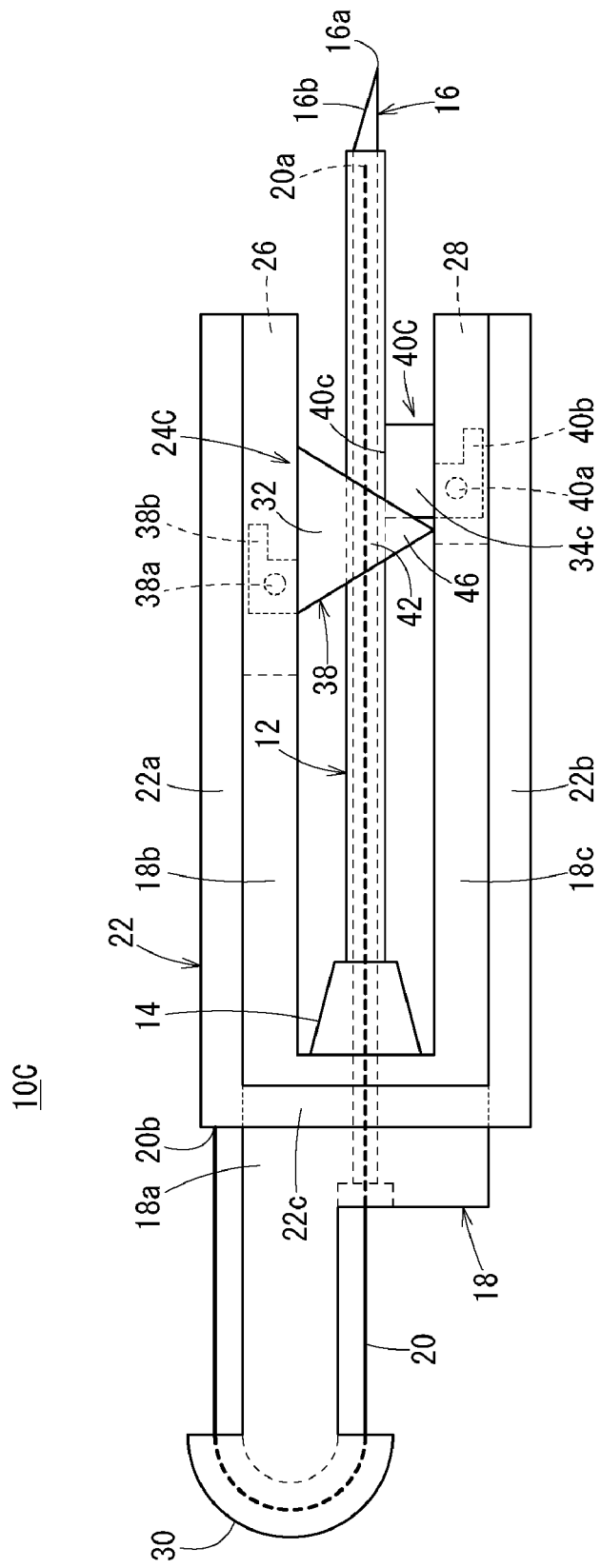
FIG. 8 is a schematic side view of a catheter assembly according to a third embodiment of the present invention.
Figure 9:
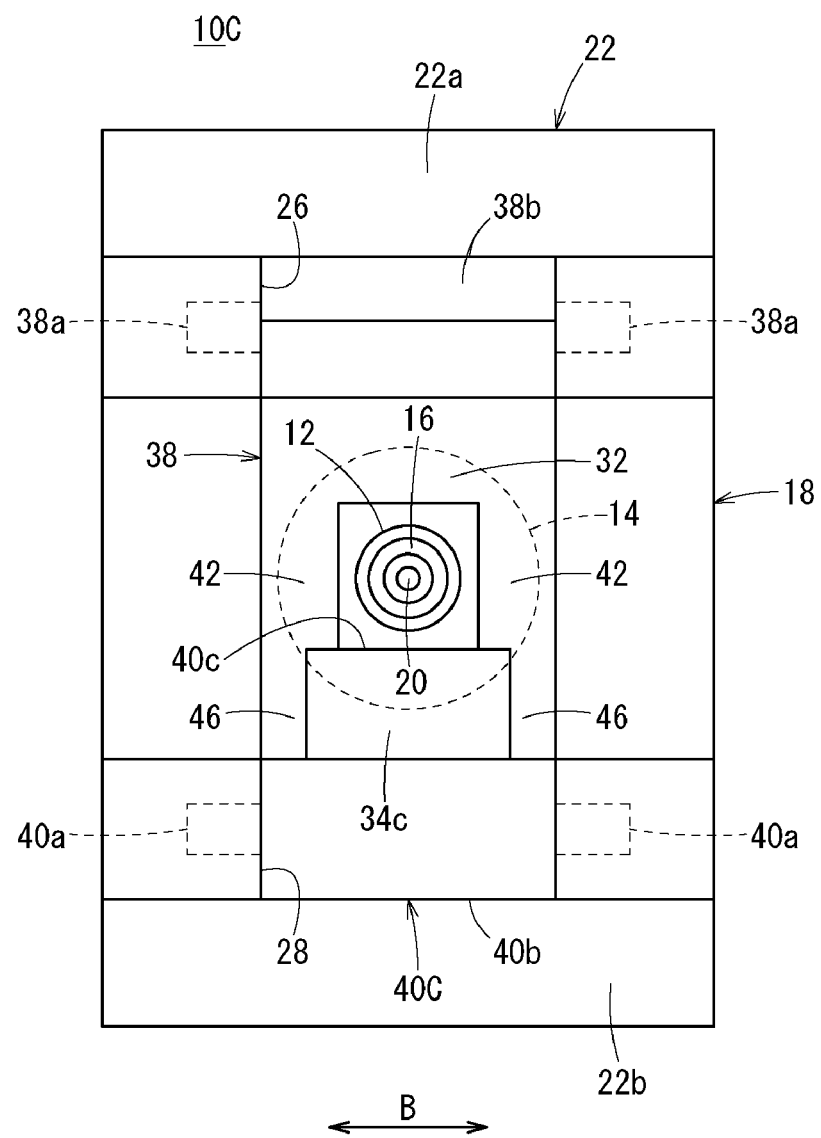
FIG. 9 is a front view of the catheter assembly illustrated in FIG. 8.

A deflection suppressing mechanism 24C of a catheter assembly 10C according to a third embodiment illustrated in FIG. 8 includes the first deflection suppressing member 38 and a second deflection suppressing member 40C having a lower deflection suppressing portion 34c. As illustrated in FIG. 9, the first deflection suppressing member 38 includes a pair of fitting walls 46, which oppose each other, in lower portions of the lateral deflection suppressing portions 42. The second deflection suppressing member 40C is separably fitted to inner surfaces of the pair of fitting walls 46. A fitting force thereof is set to such a magnitude that the fitting of the first deflection suppressing member 38 and the second deflection suppressing member 40C is released even if a user does not excessively apply a force during an advancement operation of the catheter 12.

The second deflection suppressing member 40C is fitted to the first deflection suppressing member 38 to be restricted from moving downward in a state where restriction on the first deflection suppressing member 38 and the second deflection suppressing member 40C performed by the guide wire operation member 22 is released before the catheter hub 14 abuts on the first deflection suppressing member 38 and the second deflection suppressing member 40C.

According to the catheter assembly 10C, the deflection suppressing mechanism 24C suppresses the deflection of the inner needle 16 during a puncturing operation. According to the catheter assembly 10C, the second deflection suppressing member 40C is prevented from rotating downward by its own weight before the catheter hub 14 abuts on the second deflection suppressing member 40C. As a result, it is possible to maintain a function of supporting the inner needle 16 from the lower side even after the advancement operation of the guide wire 20 and to favorably suppress the downward deflection of the inner needle 16.

Fourth Embodiment

Figure 10:
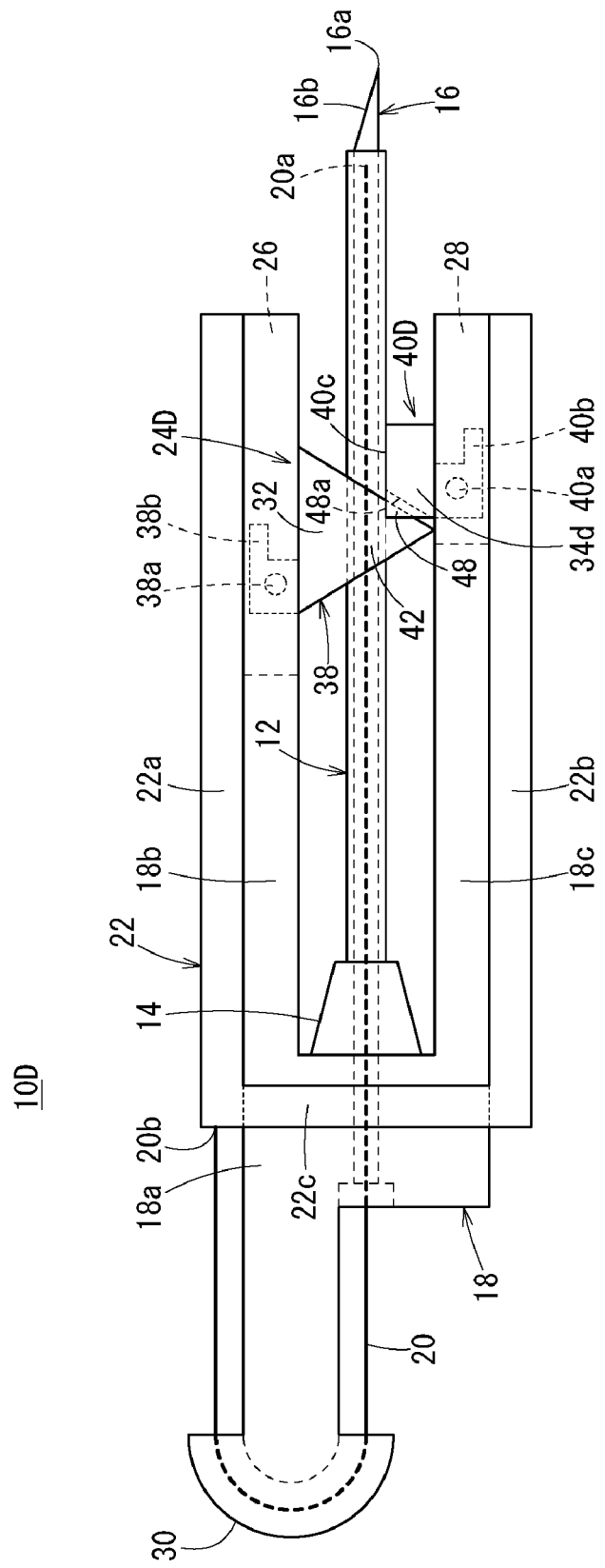
FIG. 10 is a schematic side view of a catheter assembly according to a fourth embodiment of the present invention.
Figure 11:
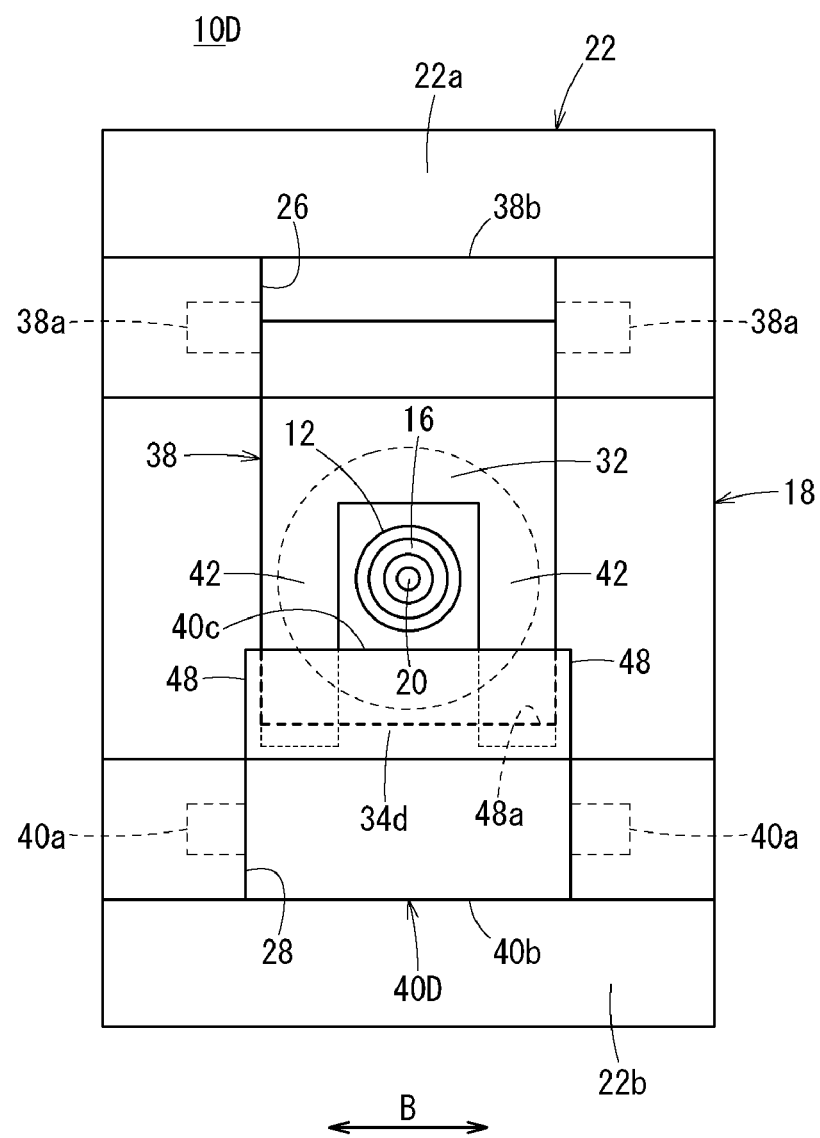
FIG. 11 is a front view of the catheter assembly illustrated in FIG. 10.

A deflection suppressing mechanism 24D of a catheter assembly 10D according to a fourth embodiment illustrated in FIG. 10 includes the first deflection suppressing member 38 and a second deflection suppressing member 40D. As illustrated in FIG. 11, the second deflection suppressing member 40D includes a pair of fitting walls 48 opposing each other. A recess notch 48a is provided between the pair of fitting walls 48. Inner surfaces of the pair of fitting walls 48 are separably fitted to the first deflection suppressing member 38 (the first deflection suppressing member 38 is fitted to the notch 48a). A fitting force thereof is set to such a magnitude that the fitting of the first deflection suppressing member 38 and the second deflection suppressing member 40D is released even if a user does not excessively apply a force during an advancement operation of the catheter 12.

The second deflection suppressing member 40D is fitted to the first deflection suppressing member 38 to be restricted from moving downward in a state where restriction on the first deflection suppressing member 38 and the second deflection suppressing member 40D performed by the guide wire operation member 22 is released before the catheter hub 14 abuts on the first deflection suppressing member 38 and the second deflection suppressing member 40D.

According to the catheter assembly 10D, the deflection suppressing mechanism 24D suppresses deflections of the inner needle 16 in the vertical and lateral directions during a puncturing operation. According to the catheter assembly 10D, the second deflection suppressing member 40D is prevented from rotating downward by its own weight before the catheter hub 14 abuts on the second deflection suppressing member 40D. As a result, it is possible to maintain a function of supporting the inner needle 16 from the lower side even after the advancement operation of the guide wire 20 and to favorably suppress the downward deflection of the inner needle 16.

Fifth Embodiment

Figure 12:
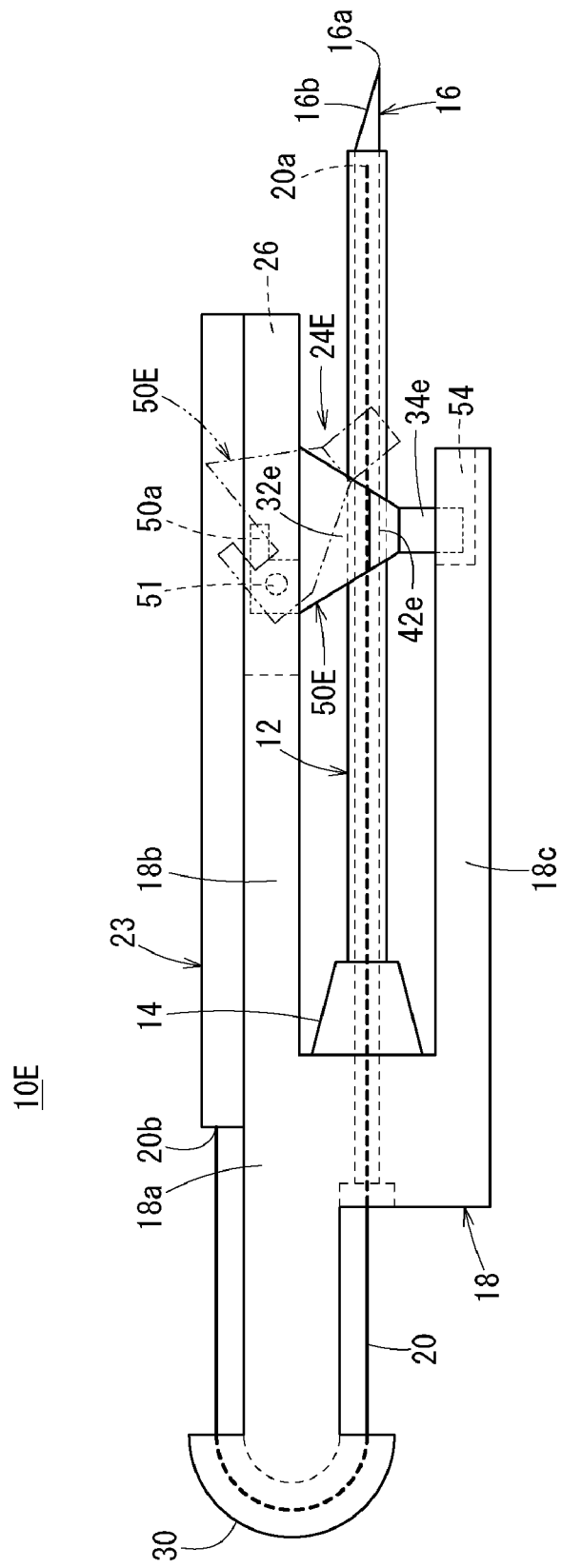
FIG. 12 is a schematic perspective view of a catheter assembly according to a fifth embodiment of the present invention.

A deflection suppressing mechanism 24E of a catheter assembly 10E according to a fifth embodiment illustrated in FIG. 12 includes a deflection suppressing member 50E movably supported by the needle hub 18. The deflection suppressing member 50E integrally includes: an upper deflection suppressing portion 32e positioned on an upper side of the inner needle 16; a pair of lateral deflection suppressing portions 42e positioned on left and right sides of the inner needle 16; and lower deflection suppressing portions 34e positioned on a lower side of the inner needle 16. The deflection suppressing member 50E is configured to be expandable in the lateral direction and is supported by the upper extension portion 18b to be rotatable about an axis (a shaft 51) in a width direction such that expansion is restricted by a groove-like expansion restriction portion 54 (hereinafter, referred to as an "expansion restriction groove 54") provided in the lower extension portion 18c.

Figure 13:
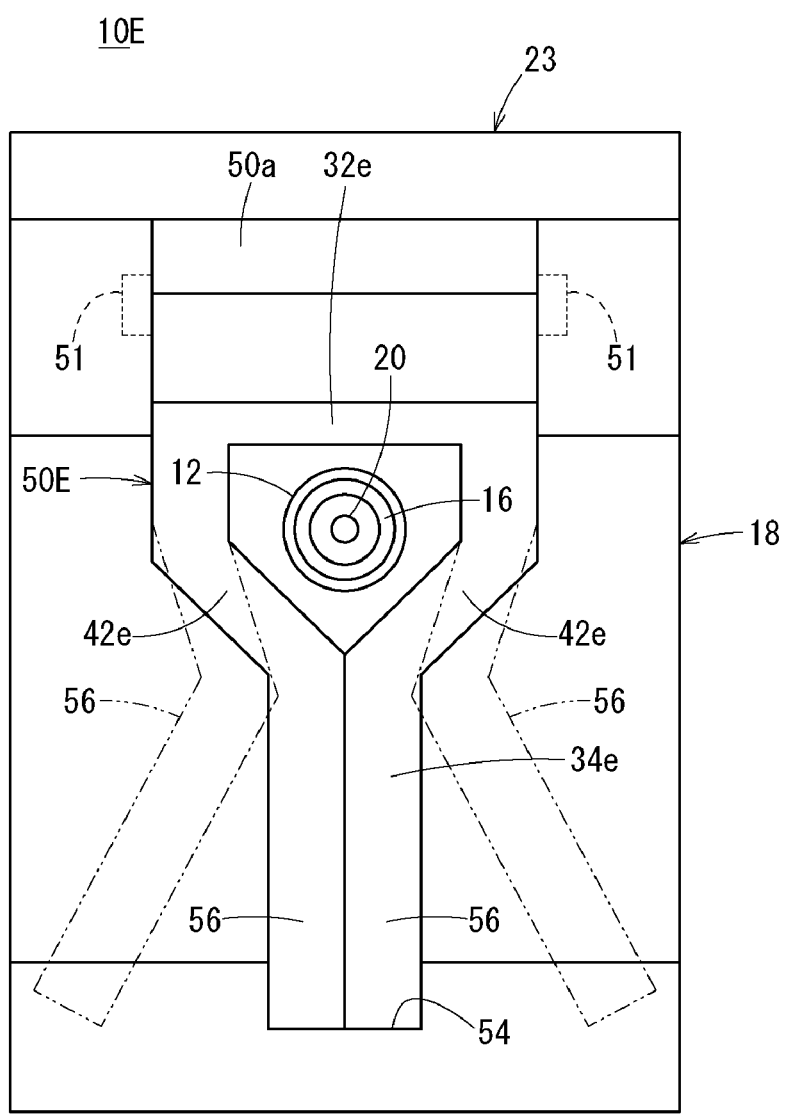
FIG. 13 is a front view of the catheter assembly illustrated in FIG. 12.

As illustrated in FIG. 13, the deflection suppressing member 50E includes first and second support arms 56 constituting the lateral deflection suppressing portions 42e and the lower deflection suppressing portions 34e. The pair of support arms 56 can be elastically deformed in the lateral direction, and are expanded in a natural state. In an initial state of the catheter assembly 10E, the lower end portions (free end portions) of the pair of support arms 56 are inserted into the expansion restriction groove 54 formed in a groove shape in the lower extension portion 18c so that the expansion of the pair of support arms 56 is restricted (blocked).

The deflection suppressing member 50E includes a restricting abutment portion 50a that is the same as the first restricting abutment portion 38b (see FIG. 1 and the like). In the catheter assembly 10E, a guide wire operation member 23 is arranged on an upper surface of the upper extension portion 18b instead of the guide wire operation member 22 (see FIG. 1 and the like). In the initial state illustrated in FIG. 12, an upward rotation of the deflection suppressing member 50E is restricted by the guide wire operation member 23.

Incidentally, the deflection suppressing member 50E may be rotatably supported by the lower extension portion 18c, and the expansion thereof may be restricted by the expansion restriction groove 54 provided in the upper extension portion 18b.

According to the catheter assembly 10E, the deflection suppressing mechanism 24E suppresses deflections of the inner needle 16 in the vertical and lateral directions during a puncturing operation. When the guide wire operation member 23 is moved in the proximal direction in order to advance the guide wire 20, the restriction on the upward rotation of the deflection suppressing member 50E performed by the guide wire operation member 23 is released.

When the catheter hub 14 is moved in the distal direction to insert the catheter 12 into the blood vessel after the advancement of the guide wire 20, the deflection suppressing member 50E is rotated along with the advancement of the catheter hub 14. Specifically, the deflection suppressing member 50E is pushed in the distal direction by the catheter hub 14 so that the deflection suppressing member 50E rotates upward as indicated by virtual lines in FIG. 12. When lower ends of the pair of support arms 56 are disengaged from the expansion restriction groove 54 along with the rotation of the deflection suppressing member 50E, the restriction on the expansion performed by the expansion restriction groove 54 is released. As a result, as indicated by virtual lines in FIG. 13, the pair of support arms 56 is expanded by an elastic restoring force.

As the deflection suppressing member 50E is further pushed in the distal direction by the catheter hub 14, the deflection suppressing member 50E rotates upward while being pushed by the catheter hub 14. In this case, the pair of support arms 56 is expanded, and thus, can be rotated toward an upper side of the catheter 12 and retracted from the catheter 12 so as to allow the catheter hub 14 to pass in the distal direction.

According to the catheter assembly 10E configured in this manner, it is possible to reduce the number of parts constituting the deflection suppressing mechanism 24E and to simplify a structure. In addition, when the catheter hub 14 is moved in the distal direction in order to insert the catheter 12 into the blood vessel, the catheter hub 14 can be smoothly passed in the distal direction through the deflection suppressing mechanism 24E.

Incidentally, the catheter assembly 10E is configured such that the catheter hub 14 directly pushes the deflection suppressing member 50E to rotate the deflection suppressing member 50E. Instead of such a configuration, it may be configured such that another member moves along with advancement of the catheter hub 14 and the other member rotates the deflection suppressing member 50E.

Sixth Embodiment

Figure 14:
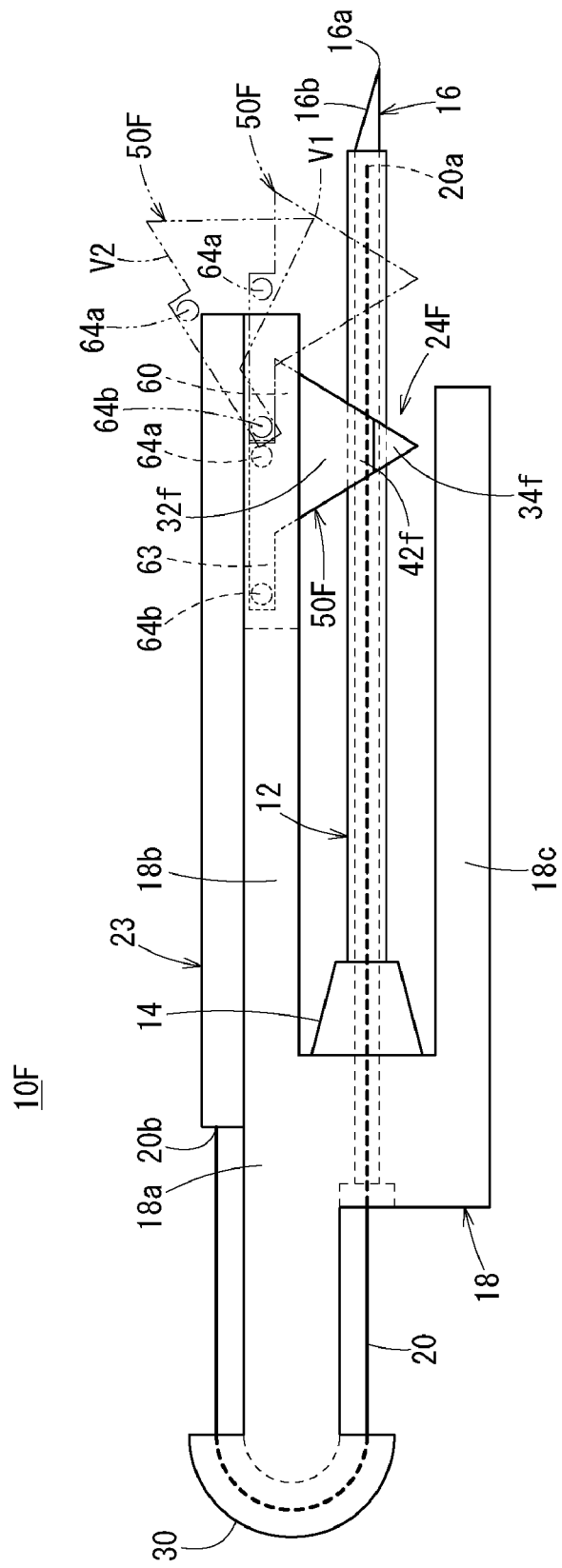
FIG. 14 is a schematic side view of a catheter assembly according to a sixth embodiment of the present invention.

A deflection suppressing mechanism 24F of a catheter assembly 10F according to a sixth embodiment illustrated in FIG. 14 includes a deflection suppressing member 50F movably supported by the needle hub 18. The deflection suppressing member 50F integrally includes: an upper deflection suppressing portion 32*f* positioned on an upper side of the inner needle 16; a pair of lateral deflection suppressing portions 42*f* positioned on left and right sides of the inner needle 16; and lower deflection suppressing portions 34*f* positioned on a lower side of the inner needle 16.

The deflection suppressing member 50F is configured to be expandable in the lateral direction and is supported by the needle hub 18 to be slidable in the axial direction such that expansion is restricted by an expansion restriction portion 60 provided in the upper extension portion 18*b*.

Figure 15:
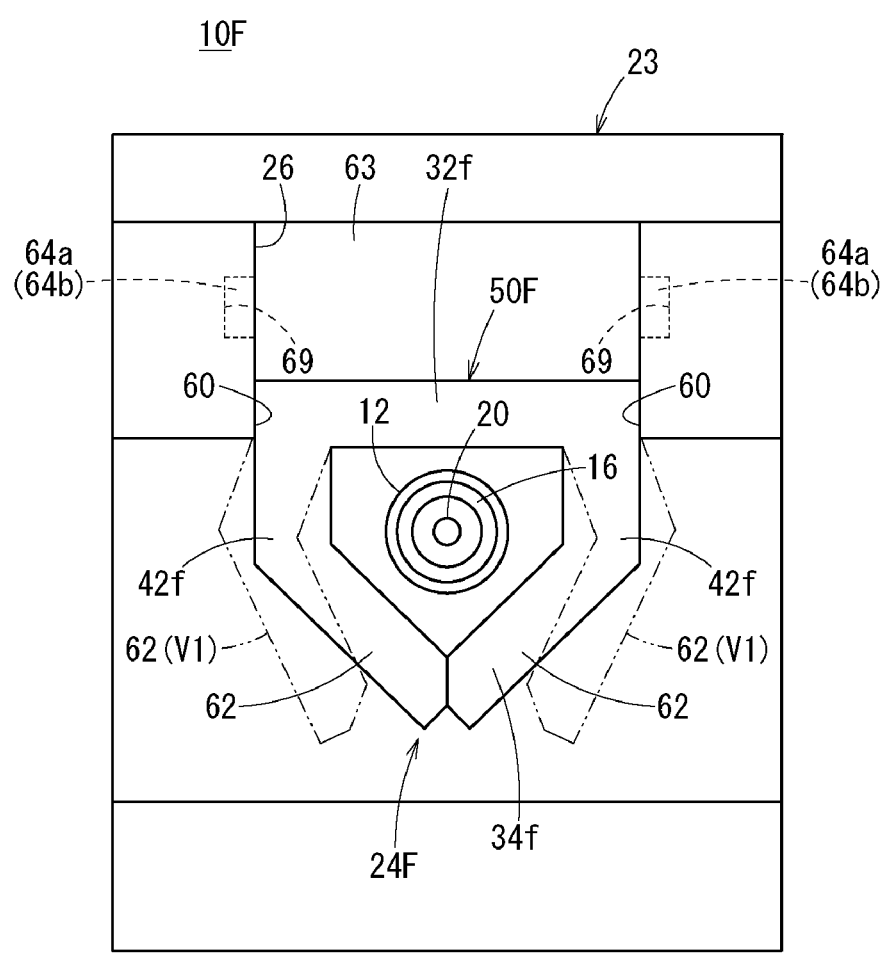
FIG. 15 is a front view of the catheter assembly illustrated in FIG. 14.

As illustrated in FIG. 15, the deflection suppressing member 50F includes first and second support arms 62 constituting the lateral deflection suppressing portions 42*f* and the lower deflection suppressing portions 34*f*. The pair of support arms 62 can be elastically deformed in the lateral direction, and is expanded in a natural state. In an initial state of the catheter assembly 10F, the pair of support arms 62 is inserted into the expansion restriction portion 60, which is a part of the first slit 26, so that the expansion of the pair of support arms 62 is restricted (blocked).

The deflection suppressing member 50F includes a slide portion 63 arranged in the first slit 26 to be slidable in the axial direction. As illustrated in FIG. 14, guide protrusions 64*a* and 64*b* are provided at both ends in the width direction on the distal side and the proximal side of the slide portion 63. As illustrated in FIG. 15, the guide protrusions 64*a* and 64*b* are slidably inserted in a guide groove 69 formed on a surface of the upper extension portion 18*b* facing the first slit 26. The guide groove 69 extends along an extending direction of the upper extension portion 18*b*.

Incidentally, the deflection suppressing member 50F may be rotatably supported by the lower extension portion 18*c*, the expansion restriction portion 60 may be configured as a part of the second slit 28, and the expansion thereof may be restricted by the expansion restriction portion 60.

According to the catheter assembly 10F, the deflection suppressing mechanism 24F suppresses deflections of the inner needle 16 in the vertical and lateral directions during a puncturing operation. When the catheter hub 14 is moved in the distal direction to insert the catheter 12 into the blood vessel after the advancement of the guide wire 20, the deflection suppressing member 50F moves in the distal direction along with the advancement of the catheter hub 14. Specifically, the deflection suppressing member 50F is pushed to advance in the distal direction by the catheter hub 14.

When the deflection suppressing member 50F advances and the guide protrusion 64*a* on the distal side moves to the distal side of the upper extension portion 18*b* as in the deflection suppressing member 50F indicated by a virtual line V1 in FIG. 14, the pair of support arms 56 is disengaged from the expansion restriction portion 60 so that the restriction on the expansion by the expansion restriction portion 60 is released. As a result, as indicated by virtual lines V1 in FIG. 15, the pair of support arms 62 is expanded by an elastic restoring force.

As the deflection suppressing member 50F is further pushed in the distal direction by the catheter hub 14, the deflection suppressing member 50F rotates upward while being pushed by the catheter hub 14 as indicated by a virtual line V2 in FIG. 14. In this case, the pair of support arms 62 is expanded, and thus, can be rotated toward an upper side of the catheter 12 and retracted from the catheter 12 so as to allow the catheter hub 14 to pass in the distal direction.

According to the catheter assembly 10F configured in this manner, it is possible to reduce the number of parts constituting the deflection suppressing mechanism 24F and to simplify a structure. In addition, when the catheter hub 14 is moved in the distal direction in order to insert the catheter 12 into the blood vessel, the catheter hub 14 can be smoothly passed in the distal direction through the deflection suppressing mechanism 24F.

Incidentally, the catheter assembly 10F is configured such that the catheter hub 14 directly pushes the deflection suppressing member 50F to advance and rotate the deflection suppressing member 50F. Instead of such a configuration, it may be configured such that another member moves along with advancement of the catheter hub 14 and the other member advances and rotates the deflection suppressing member 50F.

Seventh Embodiment

Figure 16:
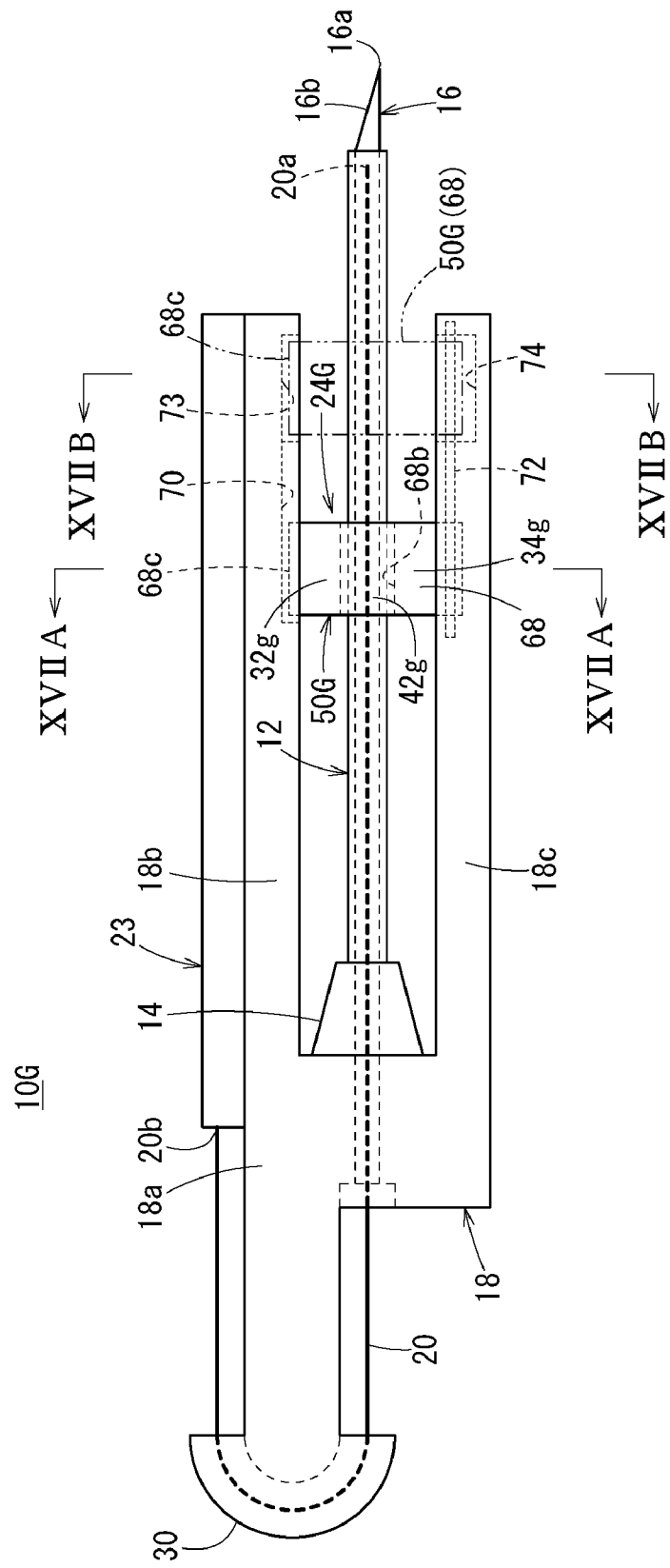
FIG. 16 is a schematic side view of a catheter assembly according to a seventh embodiment of the present invention.

A deflection suppressing mechanism 24G of a catheter assembly 10G according to a seventh embodiment illustrated in FIG. 16 includes a deflection suppressing member 50G movably supported by the needle hub 18. The deflection suppressing member 50G integrally includes: an upper deflection suppressing portion 32*g* positioned on an upper side of the inner needle 16; a pair of lateral deflection suppressing portions 42*g* positioned on left and right sides of the inner needle 16; and lower deflection suppressing portions 34*g* positioned on a lower side of the inner needle 16.

The deflection suppressing member 50G is configured to be expandable in the lateral direction and is supported by the needle hub 18 to be slidable in the axial direction such that expansion is restricted by a groove-like expansion restriction portion (hereinafter referred to as an "expansion restriction groove 70") provided in the upper extension portion 18*b*. The deflection suppressing member 50G moves in the distal direction along with advancement of the catheter hub 14. Specifically, the deflection suppressing member 50G is pushed by the catheter hub 14 in the distal direction so that the deflection suppressing member 50G moves in the distal direction. The restriction on the expansion by the expansion restriction groove 70 is released along with the movement of the deflection suppressing member 50G in the distal direction.

Figure 17A:
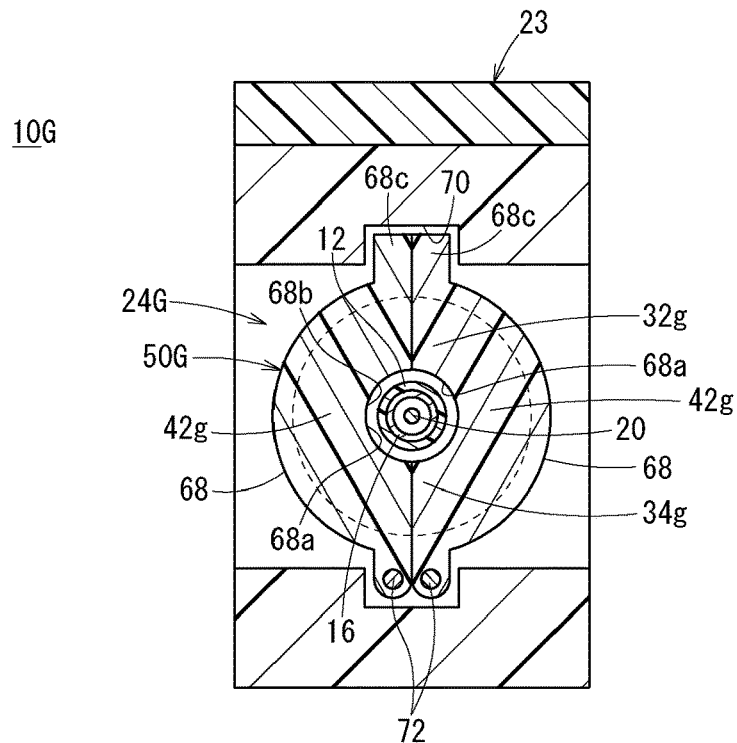
FIG. 17A is a cross-sectional view along line XVIIA-XVIIA in FIG. 16.

As illustrated in FIG. 17A, the deflection suppressing member 50G includes first and second support members 68 rotatably supported by one side of the lower extension portion 18c. The first and second support members 68 is allowed to rotate in opposite directions to be expanded along with movement in the distal direction. Each of the support members 68 is configured in a semicircular arc shape. Each of the support members 68 includes an arc-shaped recess portion 68a, and a support hole 68b penetrating in the axial direction is formed by the two recess portions 68a.

As illustrated in FIGS. 16 and 17A, lower ends of the pair of support members 68 are supported by two support pins 72, arranged in the lower extension portion 18c in parallel to the inner needle 16, so as to be slidable in the axial direction and rotatable about the support pins 72, respectively. As illustrated in FIG. 17A, in an initial state of the catheter assembly 10G, engagement protrusions 68c provided on upper portions of the pair of support members 68 are inserted into the expansion restriction groove 70 formed in the upper extension portion 18b so that the expansion of the pair of support members 68 is restricted (blocked).

Figure 17B:
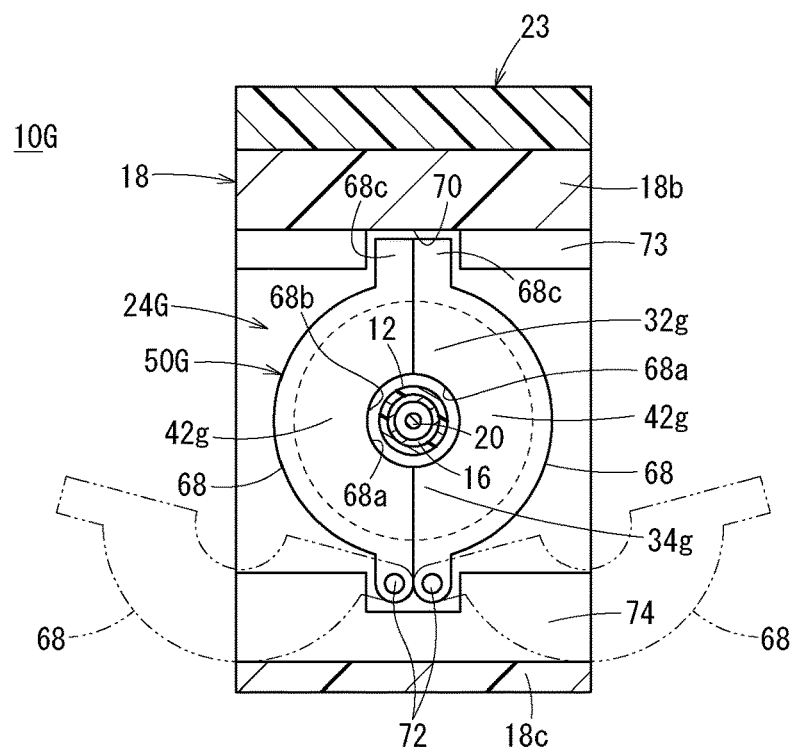
FIG. 17B is a cross-sectional view along line XVIIB-XVIIB in FIG. 16.

As illustrated in FIG. 17B, a restriction release groove 73 extending in a width direction of the upper extension portion 18b is provided on the distal side of the expansion restriction groove 70. The restriction release groove 73 communicates with the expansion restriction groove 70 and extends in the lateral direction from the distal side of the expansion restriction groove 70. A housing groove 74 capable of housing at least a part of each of the pair of support members 68 is formed at a position opposing the restriction release groove 73 in the lower extension portion 18c.

According to the catheter assembly 10G, the deflection suppressing mechanism 24G suppresses deflections of the inner needle 16 in the vertical and lateral directions during a puncturing operation. When the catheter hub 14 is moved in the distal direction to insert the catheter 12 into the blood vessel after the advancement of the guide wire 20, the deflection suppressing member 50G is pushed in the distal direction by the catheter hub 14 to advance. When the engagement protrusion 68c of the support member 68 reaches the restriction release groove 73 along with the advancement of the deflection suppressing member 50G as indicated by virtual lines in FIG. 16, the restriction on the expansion by the expansion restriction groove 70 (see also FIG. 17A) is released.

Then, the deflection suppressing member 50G is further pushed in the distal direction by the catheter hub 14 so that the pair of support members 68 constituting the deflection suppressing member 50G is pushed by the catheter hub 14 to spread in the lateral direction, thereby being open to both the left and right sides with the support pin 72 as the center. In this case, the pair of support members 68 can be widely open in the lateral direction by being inserted into the housing groove 74 (see also FIG. 17B).

According to the catheter assembly 10G configured in this manner, when the catheter hub 14 is moved in the distal direction in order to insert the catheter 12 into the blood vessel, the catheter hub 14 can be smoothly passed in the distal direction through the deflection suppressing mechanism 24G.

Incidentally, the catheter assembly 10G is configured such that the catheter hub 14 directly pushes the deflection suppressing member 50G to advance the deflection suppressing member 50G. Instead of such a configuration, it may be configured such that another member moves along with advancement of the catheter hub 14 and the other member advances the deflection suppressing member 50G.

Eighth Embodiment

Figure 18:
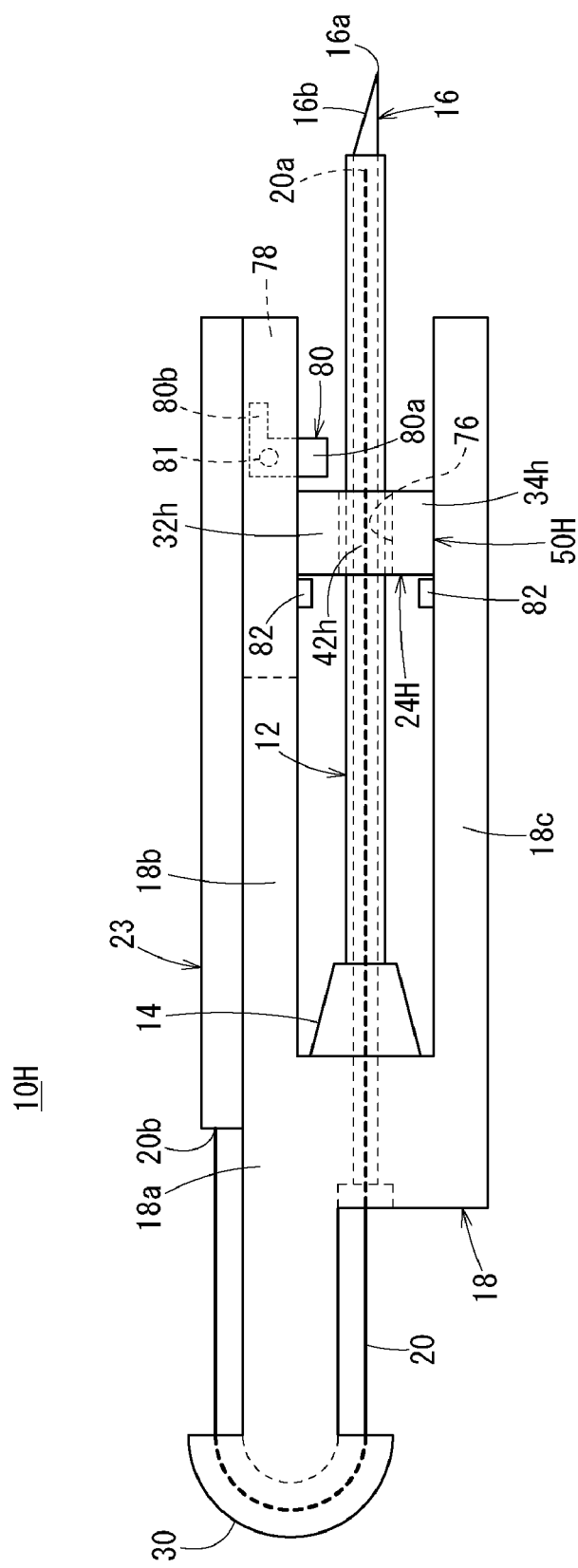
FIG. 18 is a schematic side view of a catheter assembly according to an eighth embodiment of the present invention.

A deflection suppressing mechanism 24H of a catheter assembly 10H according to an eighth embodiment illustrated in FIG. 18 includes a deflection suppressing member 50H that is supported by the needle hub 18 to be movable in the axial direction. The deflection suppressing member 50H includes a support hole 76 penetrating in the axial direction, and is formed in an annular shape in which the inner needle 16 and the catheter 12 are inserted through the support hole 76.

Figure 19:
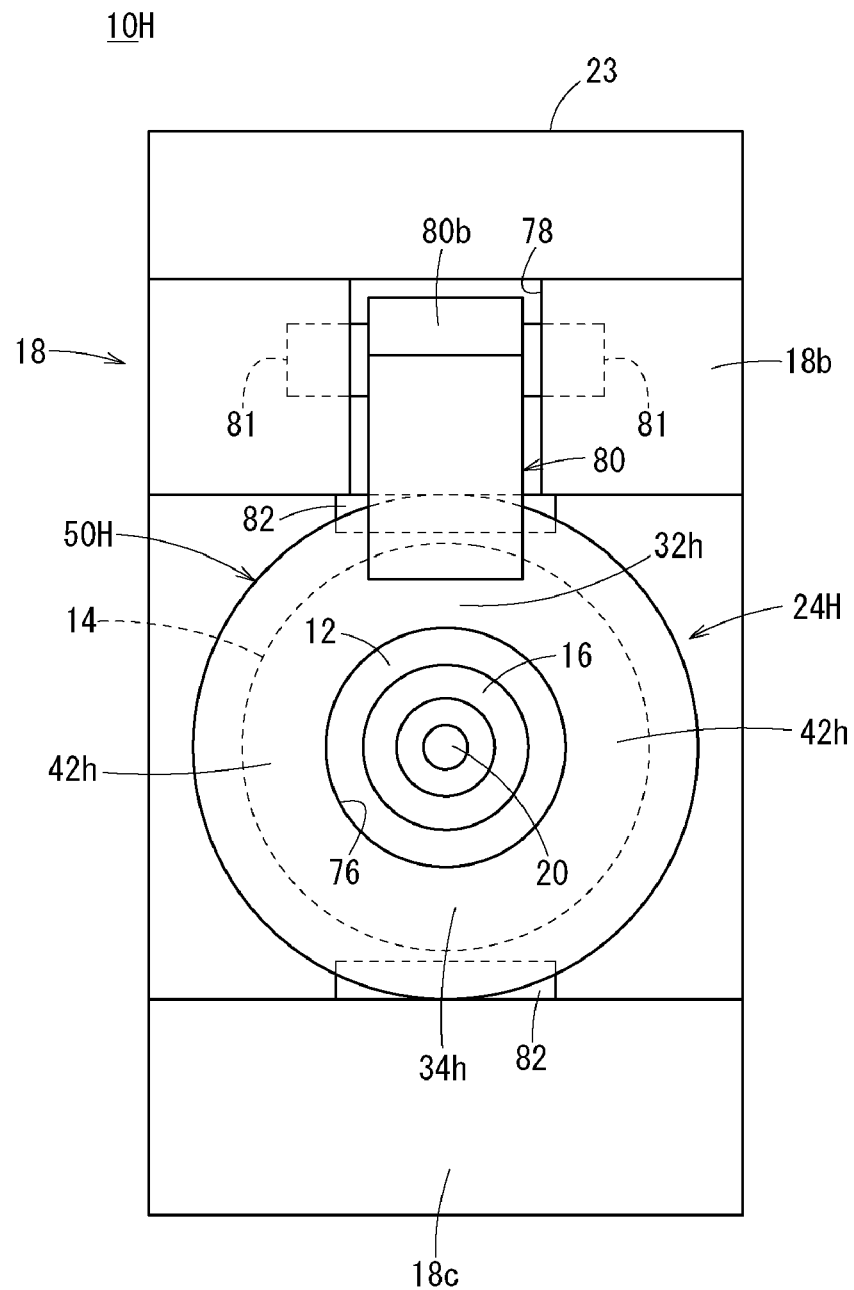
FIG. 19 is a front view of the catheter assembly illustrated in FIG. 18.

As illustrated in FIG. 19, the support hole 76 is formed in a circular shape. The support hole 76 may be formed in a non-circular shape (an elliptical shape or a polygonal shape). The deflection suppressing member 50H integrally includes: an upper deflection suppressing portion 32h positioned on an upper side of the inner needle 16; a pair of lateral deflection suppressing portions 42h positioned on left and right sides of the inner needle 16; and lower deflection suppressing portions 34h positioned on a lower side of the inner needle 16. The deflection suppressing member 50H surrounds the catheter 12 over the entire circumference.

A slit 78 penetrating in the vertical direction is formed at the distal portion of the upper extension portion 18b. The slit 78 is provided with a stopper 80 that restricts the movement of the deflection suppressing member 50H in the distal direction. The stopper 80 is rotatably supported by the upper extension portion 18b via a shaft 81. A locking portion 80a locking the deflection suppressing member 50H is provided at one end side of the stopper 80. A restricting abutment portion 80b is provided at the other end side of the stopper 80.

In a state where the restricting abutment portion 80b opposes the guide wire operation member 23, the stopper 80 is restricted from rotating, and the locking portion 80a protrudes downward from a lower surface of the upper extension portion 18b. As a result, the movement of the deflection suppressing member 50H in the distal direction is restricted. Incidentally, a locking protrusion 82, which inhibits the deflection suppressing member 50H from moving in the proximal direction, is provided on the proximal side of the deflection suppressing member 50H. The locking protrusion 82 may be integrally molded with the needle hub 18.

According to the catheter assembly 10H, the deflection suppressing mechanism 24H suppresses deflections of the inner needle 16 in the vertical and lateral directions during a puncturing operation. When the skin is punctured with the catheter assembly 10H, then, the guide wire operation member 23 is moved in the proximal direction in order to advance the guide wire 20, and the distal portion of the guide wire operation member 23 is moved to the proximal side of the restricting abutment portion 80b, the stopper 80 becomes rotatable in a direction away from the inner needle 16 (a direction of releasing the restriction on the deflection suppressing member 50H).

Then, when the catheter hub 14 is moved in the distal direction to insert the catheter 12 into the blood vessel, the deflection suppressing member 50H is pushed in the distal direction by the catheter hub 14 to advance. At this time, the catheter hub 14 is inserted into the support hole 76 of the deflection suppressing member 50H (the catheter hub 14 is fitted to the deflection suppressing member 50H).

Figure 20:
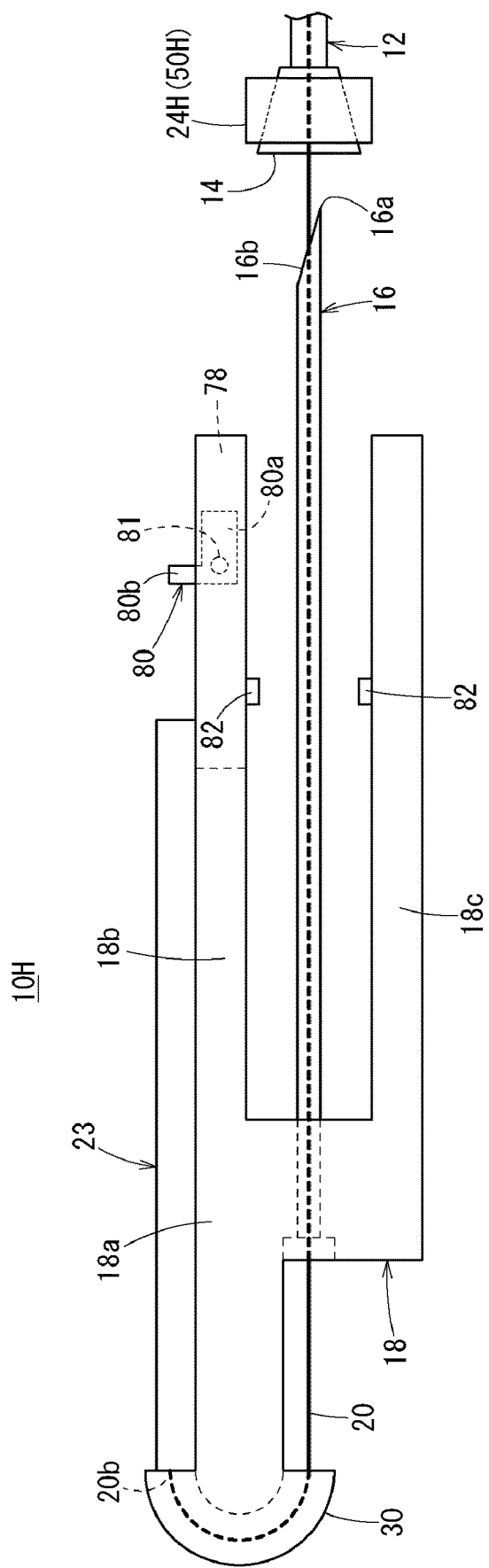
FIG. 20 is an explanatory view of a function of the catheter assembly illustrated in FIG. 18.

Because the stopper 80 is rotatable, the stopper 80 rotates by being pushed in the distal direction along with the advancement of the deflection suppressing member 50H. When the deflection suppressing member 50H further advances, the deflection suppressing member 50H is separated from the needle hub 18 in the distal direction in the state of being held by (fitted to) the catheter hub 14 as illustrated in FIG. 20.

According to the catheter assembly 10H configured in this manner, the deflection suppressing member 50H is pushed in the distal direction by the catheter hub 14 to be separated from the needle hub 18 along with the advancement of the catheter hub 14. Therefore, a mechanism that separates the catheter hub 14 from the needle hub 18 along with the advancement of the catheter hub 14 can be realized with a simple configuration.

Moreover, the deflection suppressing member 50H is held by the catheter hub 14 along with the advancement of the catheter hub 14. As a result, the deflection suppressing member 50H is not separated from other members alone along with withdrawal of the inner needle 16 from the catheter 12, and thus, handling in a medical field is excellent.

Further, the suppression of the deflection of the inner needle 16 is maintained until the deflection suppressing member 50H is separated from the needle hub 18. As a result, the deflection of the inner needle 16 is suppressed even at the time of removing the inner needle 16, and thus, the handling in the medical field is excellent.

Ninth Embodiment

Figure 21:
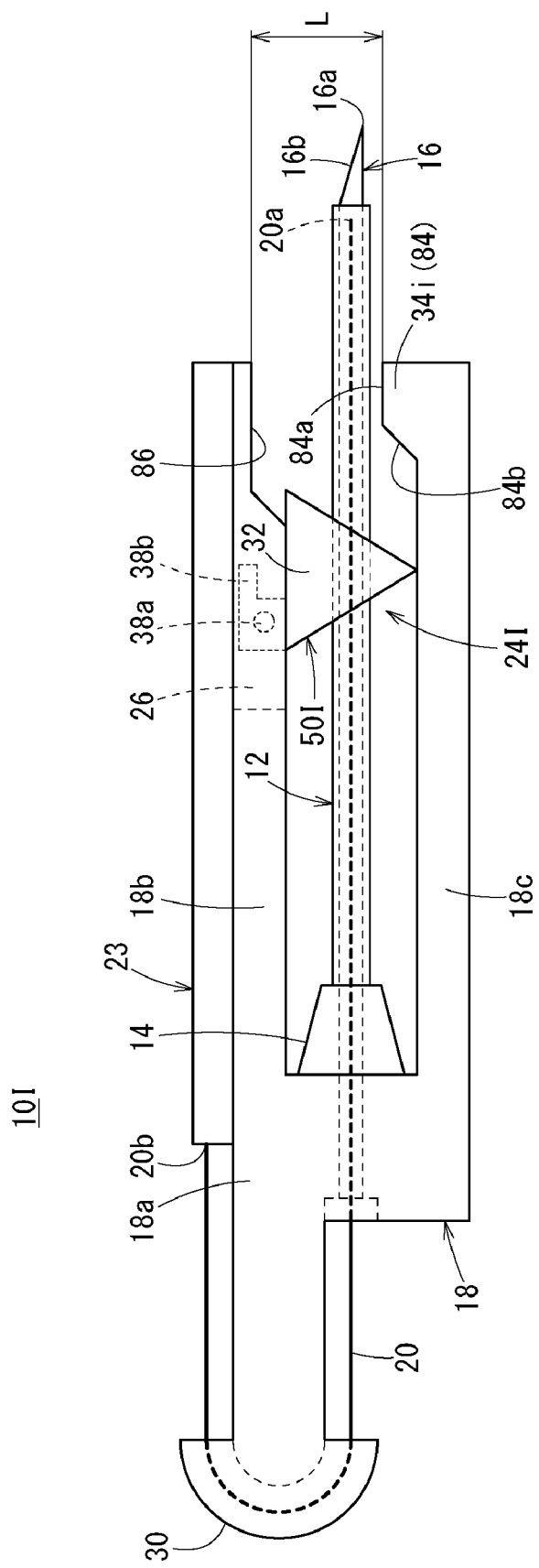
FIG. 21 is a schematic side view of a catheter assembly according to a ninth embodiment of the present invention.

A deflection suppressing mechanism 24I of a catheter assembly 10I according to a ninth embodiment illustrated in FIG. 21 includes the upper deflection suppressing portion 32 positioned on the upper side of the inner needle 16 and a lower deflection suppressing portion 34i positioned on the lower side of the inner needle 16. The upper deflection suppressing portion 32 is provided in the deflection suppressing member 50I rotatably supported by the upper extension portion 18b. The deflection suppressing member 50I is configured in the same manner as the above-described first deflection suppressing member 38 (FIG. 1).

The lower deflection suppressing portion 34i is a protrusion 84 provided on the lower extension portion 18c. In FIG. 21, the protrusion 84 protrudes from the lower extension portion 18c toward the upper extension portion 18b on the distal side of the deflection suppressing member 50I. The protrusion 84 includes: a support face 84a in proximity to (or in contact with) the catheter 12; and an inclination face 84b that is adjacent to the proximal side of the support face 84a and inclined to approach the inner needle 16 in the distal direction.

A notch 86 recessed upward is provided at a position opposing the lower deflection suppressing portion 34i on a lower surface of the upper extension portion 18b. A distance L between the notch 86 and the lower deflection suppressing portion 34i is set to a size that allows the catheter hub 14 to pass.

Incidentally, the lower deflection suppressing portion 34i may be arranged at the same axial position as the deflection suppressing member 50I, or on the proximal side of the deflection suppressing member 50I.

According to the catheter assembly 10I, the deflection suppressing mechanism 24I suppresses deflections of the inner needle 16 in the vertical and lateral directions during a puncturing operation. When the skin is punctured with the catheter assembly 10I, then, the guide wire operation member 23 is moved in the proximal direction in order to advance the guide wire 20, and the distal portion of the guide wire operation member 23 is moved to the proximal side of the restricting abutment portion 38b, the deflection suppressing member 50I becomes rotatable upward.

Then, when the catheter hub 14 is moved in the distal direction to insert the catheter 12 into the blood vessel, the deflection suppressing member 50I rotates upward while being pushed in the distal direction by the catheter hub 14.

When the catheter hub 14 is further advanced, the catheter hub 14 passes between the upper extension portion 18b and the lower extension portion 18c (between the notch 86 and the protrusion 84) and is separated from the needle hub 18 in the distal direction. In this case, the catheter hub 14 advances not linearly but along a shape of the space between the notch 86 and the protrusion 84. When the catheter hub 14 advances in such a shape of the space, the advancement of the catheter hub 14 is not inhibited because the inner needle 16 is deflected.

Incidentally, the upper deflection suppressing portion 32 may be provided on the upper extension portion 18b in the form of the protrusion 84, and the deflection suppressing member 50I having the lower deflection suppressing portion 34i may be rotatably provided in the lower extension portion 18c, which is different from the above configuration.

In this manner, according to the catheter assembly 10I, one of the upper deflection suppressing portion 32 and the lower deflection suppressing portion 34i is provided on the deflection suppressing member 50I rotatably supported by the needle hub 18, and the other of the upper deflection suppressing portion 32 and the lower deflection suppressing portion 34i is the protrusion 84 provided on the needle hub 18. Thus, the deflection suppressing mechanism 24I can be realized with a simple configuration.

Tenth Embodiment

Figure 22:
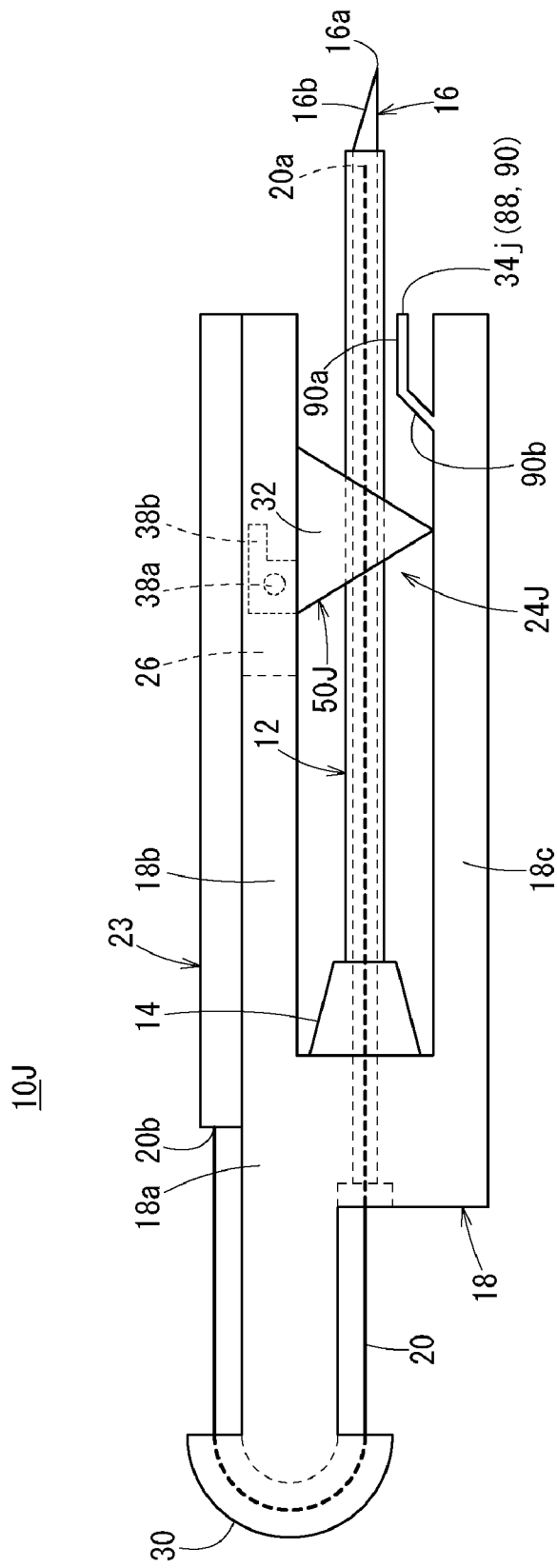
FIG. 22 is a schematic side view of a catheter assembly according to a tenth embodiment of the present invention.

A deflection suppressing mechanism 24J of a catheter assembly 10J according to a tenth embodiment illustrated in FIG. 22 includes a deflection suppressing member 50J (having the same configuration as the first deflection suppressing member 38 illustrated in FIG. 1), and a lower deflection suppressing portion 34j. The deflection suppressing mechanism 24J is obtained by replacing the lower deflection suppressing portion 34i in the deflection suppressing mechanism 24I (FIG. 21) described above with the lower deflection suppressing portion 34j of another form. The lower deflection suppressing portion 34j is also a protrusion 88 provided on the lower extension portion 18c, but has a form of an elastic piece 90 (leaf spring) that is elastically deformable in a direction away from the inner needle 16.

The elastic piece 90 includes: a support face 90a that extends along the inner needle 16 (and the catheter 12) in a natural state; and an inclined face 90b that is provided to be adjacent to the proximal side of the support face 90a and inclined to approach the inner needle 16 in the distal direction. The notch 86 is not provided on the lower surface of the distal portion of the upper extension portion 18b in the catheter assembly 10J, which is different from the catheter assembly 10I (FIG. 21).

According to the catheter assembly 10J, the deflection suppressing mechanism 24J suppresses deflections of the inner needle 16 in the vertical and lateral directions during the puncturing operation. When the skin is punctured with the catheter assembly 10J, then, the guide wire operation member 23 is moved in the proximal direction in order to advance the guide wire 20, and the distal portion of the guide wire operation member 23 is moved to the proximal side of the restricting abutment portion 38b, the deflection suppressing member 50J becomes rotatable upward.

Then, when the catheter hub 14 is moved in the distal direction to insert the catheter 12 into the blood vessel, the deflection suppressing member 50J rotates upward while being pushed in the distal direction by the catheter hub 14.

When the catheter hub 14 is further advanced, the catheter hub 14 passes between distal portions of the upper extension portion 18b and the lower extension portion 18c while pushing down the elastic piece 90 against an elastic force of the elastic piece 90 and is separated from the needle hub 18 in the distal direction. In this manner, the passage of the catheter hub 14 is secured by the elastic deformation of the elastic piece 90, and thus, the catheter hub 14 can be separated from the needle hub 18 without any problem.

Incidentally, the lower deflection suppressing portion 34j may be arranged at the same axial position as the deflection suppressing member 50J, or on the proximal side of the deflection suppressing member 50J.

Eleventh Embodiment

Figure 23:
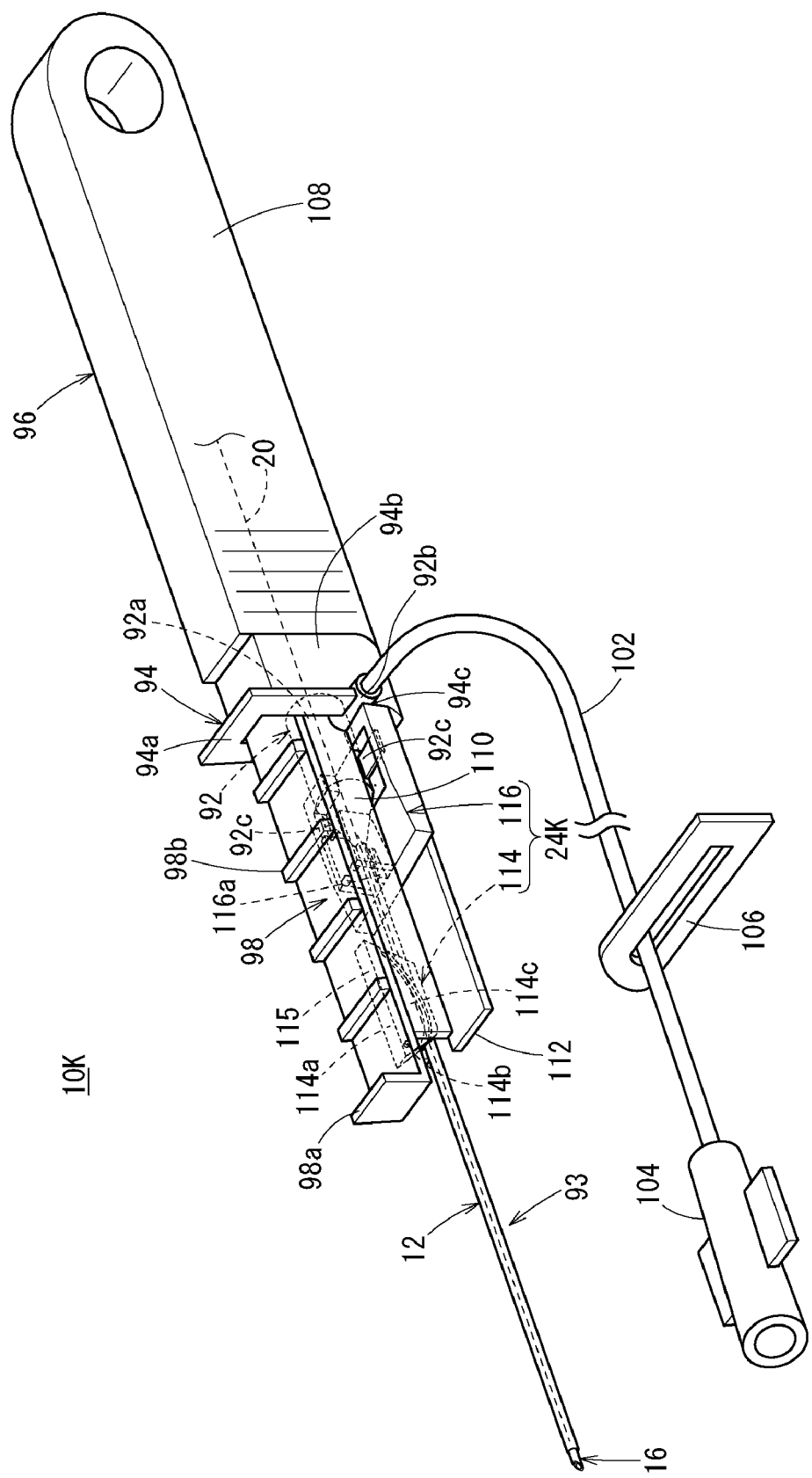
FIG. 23 is a perspective view of a catheter assembly according to an eleventh embodiment of the present invention.

A catheter assembly 10K according to an eleventh embodiment illustrated in FIG. 23 includes: the catheter 12; a catheter hub 92 connected to the catheter 12; a catheter release member 94 moving the catheter hub 92 in the distal direction by a predetermined distance; the inner needle 16 inserted into the catheter 12; a needle hub 96 connected to the inner needle 16; the guide wire 20 inserted into the inner needle 16; a wire operation member 98 connected to the guide wire 20; and a deflection suppressing mechanism 24K suppressing the deflection of the inner needle 16 at the time of puncture.

The catheter 12 includes: a lumen penetrating through the catheter 12 in the axial direction; a distal opening open at a distal end of the catheter 12; and a proximal opening open at a proximal end of the catheter 12.

The catheter hub 92 is fixed to the proximal portion of the catheter 12. The catheter 12 and the catheter hub 92 constitute a catheter member 93. In an initial state of the catheter assembly 10K illustrated in FIG. 23, a proximal portion of the catheter hub 92 is housed in the catheter release member 94 to be described later.

The catheter hub 92 includes: a hub body 92a connected to the catheter 12; a side port 92b protruding in a traverse direction from the hub body 92a (horizontal direction perpendicular to an axis of the hub body 92a); and a pair of wings 92c protruding in the lateral direction from the hub body 92a. One end of a soft tube 102 is connected to the side port 92b. The connector 104 is connected to the other end of the tube 102. A clamp 106 capable of opening and closing a flow path in the tube 102 is attached to the tube 102.

The catheter release member 94 is an annular member that is supported by a distal portion of a housing 108, which will be described later, of the needle hub 96, to be slidable in the front-rear direction. The catheter release member 94 is provided with a finger hook portion 94a protruding in a flange shape. A recess portion 94c open in the distal direction is provided on a side wall 94b of the catheter release member 94. The side port 92b of the catheter hub 92 protrudes in the traverse direction via the recess portion 94c.

The needle hub 96 includes: the housing 108 that functions as a grip to be gripped by the user; and an upper extension portion 110 and a lower extension portion 112 that extend parallel to each other in the distal direction from the distal portion of the housing 108. In an initial state of the catheter assembly 10K, the catheter 12 and the catheter hub 92 are arranged between the upper extension portion 110 and the lower extension portion 112.

The deflection suppressing mechanism 24K is provided at a distal portion of the needle hub 96. Specifically, the deflection suppressing mechanism 24K includes: a first deflection suppressing member 114 that includes an upper deflection suppressing portion 114a and is movably supported by the needle hub 96; and a second deflection suppressing member 116 that includes a lower deflection suppressing portion 116a and holds the catheter hub 92 in a detachable manner in the initial state.

A shaft 114b is provided in an upper portion of the first deflection suppressing member 114. The shaft 114b is pivotally supported by the upper extension portion 110. As a result, the first deflection suppressing member 114 is supported by the upper extension portion 110 so as to be rotatable about an axis that extends in the lateral direction. The shaft 114b is provided on the distal side of a central portion in the front-rear direction of the first deflection suppressing member 114.

The upper deflection suppressing portion 114a includes a sliding contact support portion 115 capable of rubbing against the catheter 12 when the catheter 12 is advanced with respect to the inner needle 16. In the initial state of the catheter assembly 10K, a distal portion of the wire operation member 98 is positioned on the distal side of the first deflection suppressing member 114. Thus, the first deflection suppressing member 114 is restricted from rotating upward by the wire operation member 98.

Figure 24:
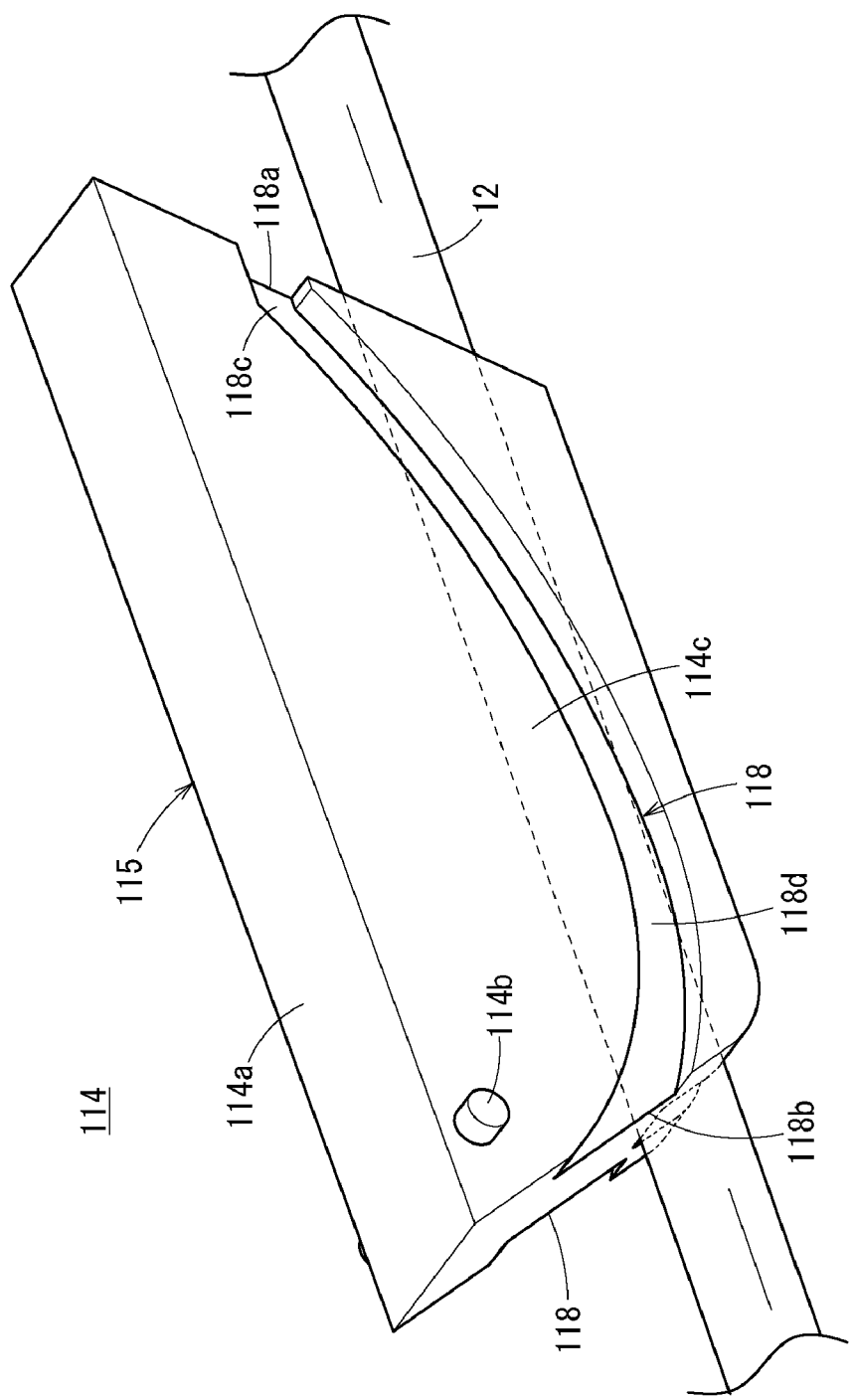
FIG. 24 is a perspective view of a first deflection suppressing member of the catheter assembly illustrated in FIG. 23.

As illustrated in FIG. 24, the sliding contact support portion 115 includes: the upper deflection suppressing portion 114a capable of supporting the catheter 12 from the upper side; and left and right traverse support portions 114c that can support the catheter 12 from the traverse direction. The traverse support portions 114c protrude downward from the left and right ends of the upper deflection suppressing portion 114a. Therefore, the sliding contact support portion 115 is formed in an inverted U shape when viewed from a longitudinal direction of the catheter assembly 10K. In the initial state of the catheter assembly 10K, a slight gap is formed between an outer surface of the catheter 12 and the sliding contact support portion 115.

The first deflection suppressing member 114 is provided with a guide portion that comes into contact with the second deflection suppressing member 116 as the second deflection suppressing member 116 moves. The guide portion in the present embodiment includes a wall provided on the first deflection suppressing member 114. A specific form including the wall is a guide groove 118 that is engageable with the second deflection suppressing member 116. In the illustrated example, a pair of the guide grooves 118 is provided on left and right side surfaces of the first deflection suppressing member 114. The pair of guide grooves 118 has a shape symmetrical in the lateral direction. Each of the guide grooves 118 includes a proximal opening 118a and a distal opening 118b. Each of the guide grooves 118 includes: an introduction portion 118c having a wall extending in parallel to the inner needle 16 in the initial state; and a direction changing portion 118d communicating with the introduction portion 118c on the distal side of the introduction portion 118c. A proximal end of the introduction portion 118c serves as the proximal opening 118a. The direction changing portion 118d is curved so as to be convex downward. A distal end of the direction changing portion 118d serves as the distal opening 118b. The guide groove 118 is provided on the lower side of the shaft 114b. The guide groove 118 includes a wall in contact with the second deflection suppressing member 116.

Figure 25:
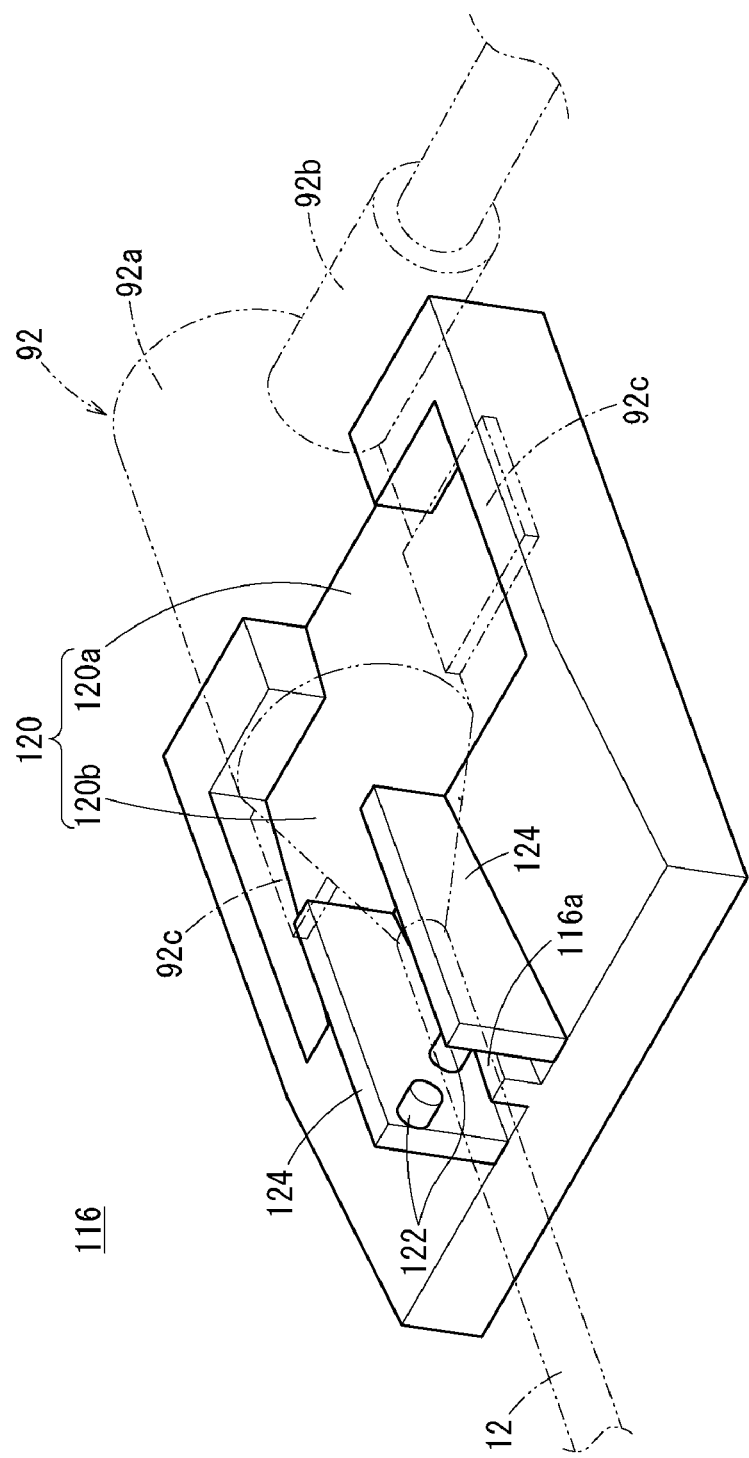
FIG. 25 is a perspective view of a second deflection suppressing member of the catheter assembly illustrated in FIG. 23.

As illustrated in FIG. 23, the second deflection suppressing member 116 is separably mounted to the catheter hub 92 in the initial state of the catheter assembly 10K. The second deflection suppressing member 116 is a catheter operation member configured to be gripped by the user to advance the catheter 12. In FIG. 25, a mounting groove 120 for housing the catheter hub 92 is provided on an upper surface of the second deflection suppressing member 116.

The mounting groove 120 includes: a body fitting portion 120*a* to which the hub body 92*a* of the catheter hub 92 is fitted; and a wing housing portion 120*b* that is provided to be adjacent to the distal side of the body fitting portion 120*a* and houses the pair of wings 92*c* of the catheter hub 92. The lower deflection suppressing portion 116*a* is provided on the distal side of the wing housing portion 120*b*. In the initial state of the catheter assembly 10K, the lower deflection suppressing portion 116*a* is positioned on the lower side of the inner needle 16.

The second deflection suppressing member 116 includes a guide portion that rotates the first deflection suppressing member 114 when the second deflection suppressing member 116 advances. The guide portion in the present embodiment includes a face in contact with a wall provided on the first deflection suppressing member 116. A specific form including the face is a guide protrusion 122. In the illustrated example, a pair of the guide protrusions 122 is provided on the distal side of the mounting groove 120 with an interval in the lateral direction. The pair of guide protrusions 122 protrudes in directions of approaching each other from inner surfaces, which oppose each other, of support plates 124 protruding upward from an upper portion of the second deflection suppressing member 116. The pair of guide protrusions 122 can enter the pair of guide grooves 118 provided in the first deflection suppressing member 114. The pair of guide protrusions 122 includes faces that come into contact with the walls of the pair of guide grooves 118 provided in the first deflection suppressing member 114.

In FIG. 23, the wire operation member 98 is an operation portion configured to perform the operation of inserting the guide wire 20 into the blood vessel prior to the operation of inserting the catheter 12 into the blood vessel of the patient. A finger hook projection 98*a* and a plurality of anti-slip ribs 98*b* are provided at a distal end of the wire operation member 98. The wire operation member 98 is supported on an upper surface of the upper extension portion 110 to be slidable in the front-rear direction. One end of the guide wire 20 is arranged near a distal end of the inner needle 16. Although not illustrated in detail, the other end of the guide wire 20 is connected to the wire operation member 98, and an intermediate portion of the guide wire 20 is folded back inside the housing 108.

Next, functions of the catheter assembly 10K configured as described above will be described.

In use of the catheter assembly 10K, a puncturing operation to puncture the patient's skin with the catheter assembly 10K is performed. In the puncturing operation, the user presses a distal portion of the catheter assembly 10K against the patient while gripping the housing 108 of the catheter assembly 10K in the initial state illustrated in FIG. 23, thereby puncturing the skin toward a puncture target blood vessel. Accordingly, the skin is punctured with the inner needle 16 and each distal portion of the catheter 12.

Next, when the user moves the wire operation member 98 in the proximal direction, the guide wire 20 whose intermediate portion has been folded back inside the housing 108 moves in the distal direction inside the inner needle 16. As a result, the guide wire 20 protrudes from the distal end of the inner needle 16 and is inserted into the blood vessel. Along with the movement of the wire operation member 98 in the proximal direction, the distal portion of the wire operation member 98 moves in the proximal direction more than the upper portion of the first deflection suppressing member 114. As a result, the restriction on the upward rotation of the first deflection suppressing member 114 performed by the wire operation member 98 is released.

In this case, the shaft 114*b* of the first deflection suppressing member 114 is provided on the distal side of the central portion in the front-rear direction of the first deflection suppressing member 114, and thus, the first deflection suppressing member 114 does not rotate even if the inner needle 16 (and the catheter 12) is bent upward. Therefore, a function of suppressing the deflection of the inner needle 16 by the first deflection suppressing member 114 can be maintained even after the wire operation member 98 is moved in the proximal direction.

Once the distal end of the guide wire 20 is inserted to the target position in the blood vessel, the user then advances the catheter release member 94 slightly (by about several mm) while fixing the position of the needle hub 96. Next, the user operates the second deflection suppressing member 116 (or may operate the tube 102) in the distal direction to advance the catheter member 93 (the catheter 12 and the catheter hub 92). Accordingly, the catheter 12 is inserted to the target position in the blood vessel. Then, the first deflection suppressing member 114 receives a force from the second deflection suppressing member 116 moving in the distal direction to rotate such that a proximal portion of the first deflection suppressing member 114 is displaced upward. As a result, the catheter hub 92 and the second deflection suppressing member 116 are allowed to be separated from the needle hub 96 in the distal direction.

Next, the user pulls the housing 108 in the proximal direction while holding the positions of the catheter member 93 and the second deflection suppressing member 116. As a result, the catheter member 93 and the second deflection suppressing member 116 completely come out of the needle hub 96, and the inner needle 16 is removed from the catheter 12 in the proximal direction. Next, the second deflection suppressing member 116 is detached from the catheter hub 92. As a result, the catheter 12 is indwelled in the patient's blood vessel.

The rotation of the first deflection suppressing member 114 along with the advancement of the second deflection suppressing member 116 will be specifically described with reference to FIGS. 26A to 27C.

Figure 26A:
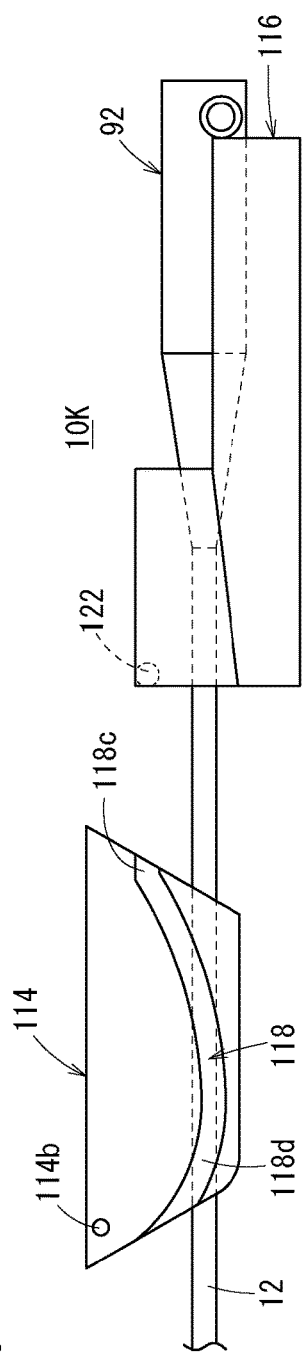
FIG. 26A is a first operation explanatory view of a deflection suppressing mechanism of the catheter assembly illustrated in FIG. 23.
Figure 26B:
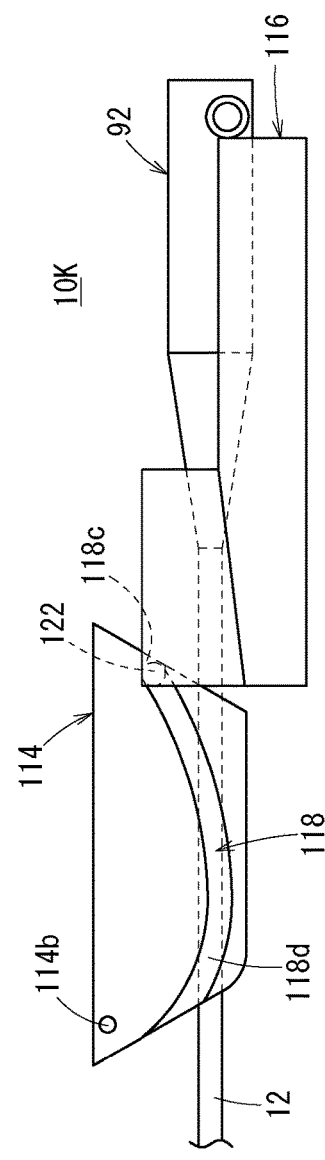
FIG. 26B is a second operation explanatory view of the deflection suppressing mechanism of the catheter assembly illustrated in FIG. 23.
Figure 26C:
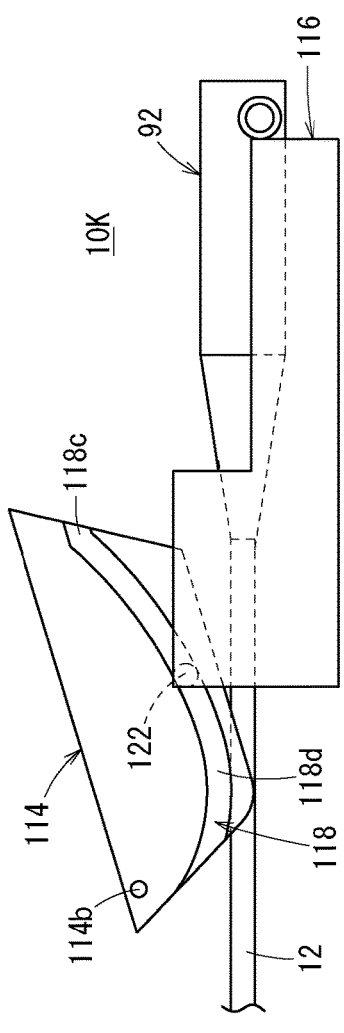
FIG. 26C is a third operation explanatory view of the deflection suppressing mechanism of the catheter assembly illustrated in FIG. 23.

In the initial state of the catheter assembly 10K, the guide protrusion 122 of the second deflection suppressing member 116 is positioned on the proximal side of the guide groove 118 of the first deflection suppressing member 114 as illustrated in FIG. 26A. When the second deflection suppressing member 116 is advanced to advance the catheter 12, the guide protrusion 122 enters the introduction portion 118*c* of the guide groove 118 as illustrated in FIG. 26B. When the second deflection suppressing member 116 further advances, the guide protrusion 122 starts to enter the direction changing portion 118*d* of the guide groove 118 so that the first deflection suppressing member 114 starts to rotate (counterclockwise in FIG. 26C) such that the proximal portion is displaced upward as illustrated in FIG. 26C. That is, the first deflection suppressing member 114 starts to rotate as the guide protrusion 122 slides along the curved direction changing portion 118*d*. A rotation angle of the first deflection suppressing member 114 increases as the second deflection suppressing member 116 further advances.

Figure 27A:
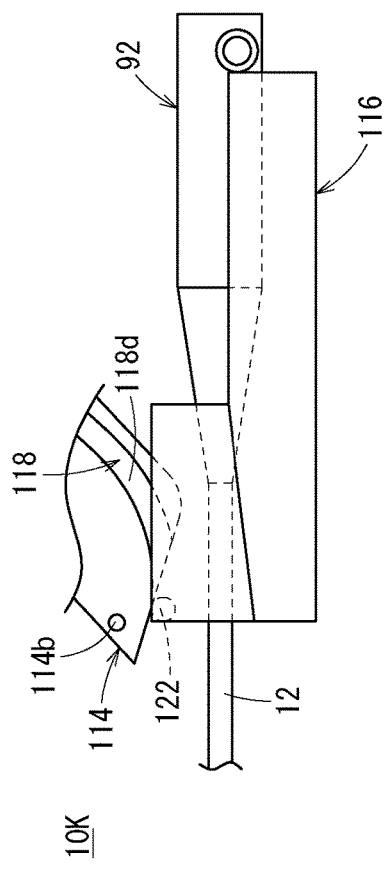
FIG. 27A is a fourth operation explanatory view of the deflection suppressing mechanism of the catheter assembly illustrated in FIG. 23.
Figure 27B:
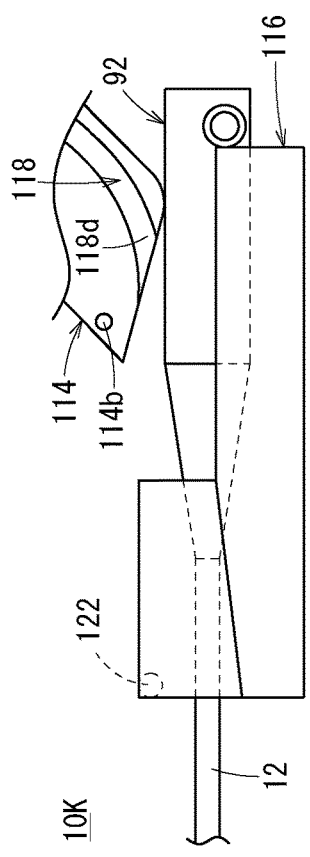
FIG. 27B is a fifth operation explanatory view of the deflection suppressing mechanism of the catheter assembly illustrated in FIG. 23.
Figure 27C:
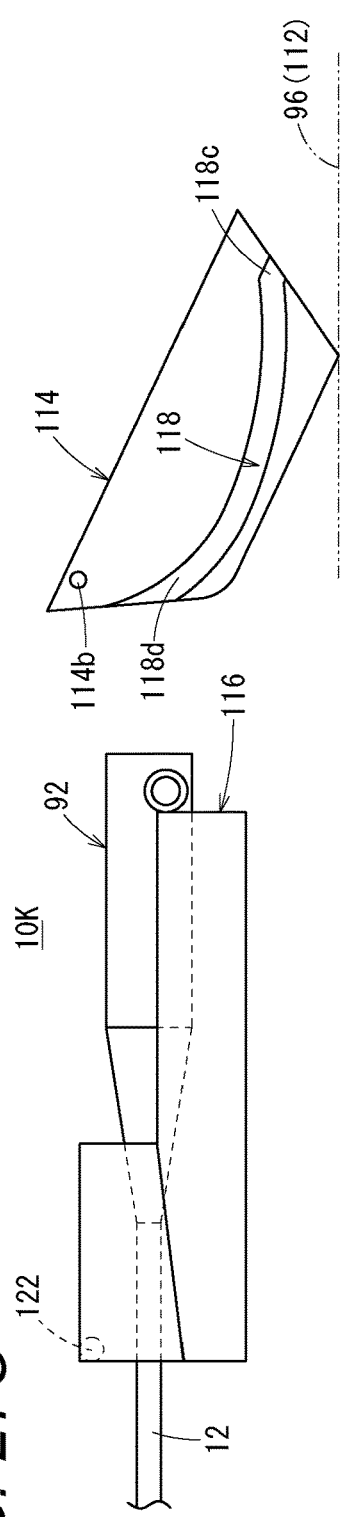
FIG. 27C is a sixth operation explanatory view of the deflection suppressing mechanism of the catheter assembly illustrated in FIG. 23.

When the second deflection suppressing member 116 further advances, the guide protrusion 122 is separated from the guide groove 118 in the distal direction as illustrated in FIG. 27A. The first deflection suppressing member 114 falls onto the catheter hub 92 by its own weight along with the separation of the guide protrusion 122 from the guide groove 118. After such a fall, the first deflection suppressing member 114 moves up and down following an outer shape of the catheter hub 92 along with the advancement of the catheter hub 92 as illustrated in FIG. 27B. Then, when the catheter hub 92 completely comes out of the needle hub 96 in the distal direction, the first deflection suppressing member 114 falls to a position to abut on the lower extension portion 112 as illustrated in FIG. 27C.

In this manner, the first deflection suppressing member 114 can be rotated upward along with the advancement of the second deflection suppressing member 116 due to the interaction between the guide protrusion 122 and the guide groove 118, and thus, the catheter hub 92 can be moved smoothly beyond the first deflection suppressing member 114 in the distal direction without any problem.

Although the present embodiment has been described with a combination of the guide groove 118 of the first deflection suppressing member 114 and the guide protrusion 122 of the second deflection suppressing member 116, a member that includes a bottom face including a curved face of the first deflection suppressing member 114, instead of the guide groove 118, and a portion to be rotated in contact with the bottom face of the first deflection suppressing member 114, instead of the guide protrusion 122, may be configured as another mode. Examples of the portion to be rotated may include a distal portion of the second deflection suppressing member 116 according to the present embodiment. More specifically, a distal portion of the support plate 124 may be used. Another example of the portion to be rotated is a distal portion of the catheter hub 92. With such a configuration, when the catheter 12 is advanced, the distal portion of the support plate 124 or the distal portion of the catheter hub 92 comes into contact with the bottom surface of the first deflection suppressing member 114 to rotate the first deflection suppressing member 114. The catheter hub 92 can be moved beyond the first deflection suppressing member 114 in the distal direction without any problem.

In the initial state, the guide protrusion 122 and the guide groove 118 may be fitted to each other. In addition, a mechanism that prevents the rotation of the first deflection suppressing member 114 caused by the wire operation member 98 is not necessarily provided.

With such a configuration, the first deflection suppressing member 114 does not rotate between the advancement of the guide wire 20 and the state where the guide protrusion 122 and the guide groove 118 are fitted to each other. In addition, the catheter 12 can be advanced even before advancing the guide wire 20. In addition, the rotation of the first deflection suppressing member 114 in the initial state can be prevented even in a product that is not provided with the guide wire 20.

Figure 28:
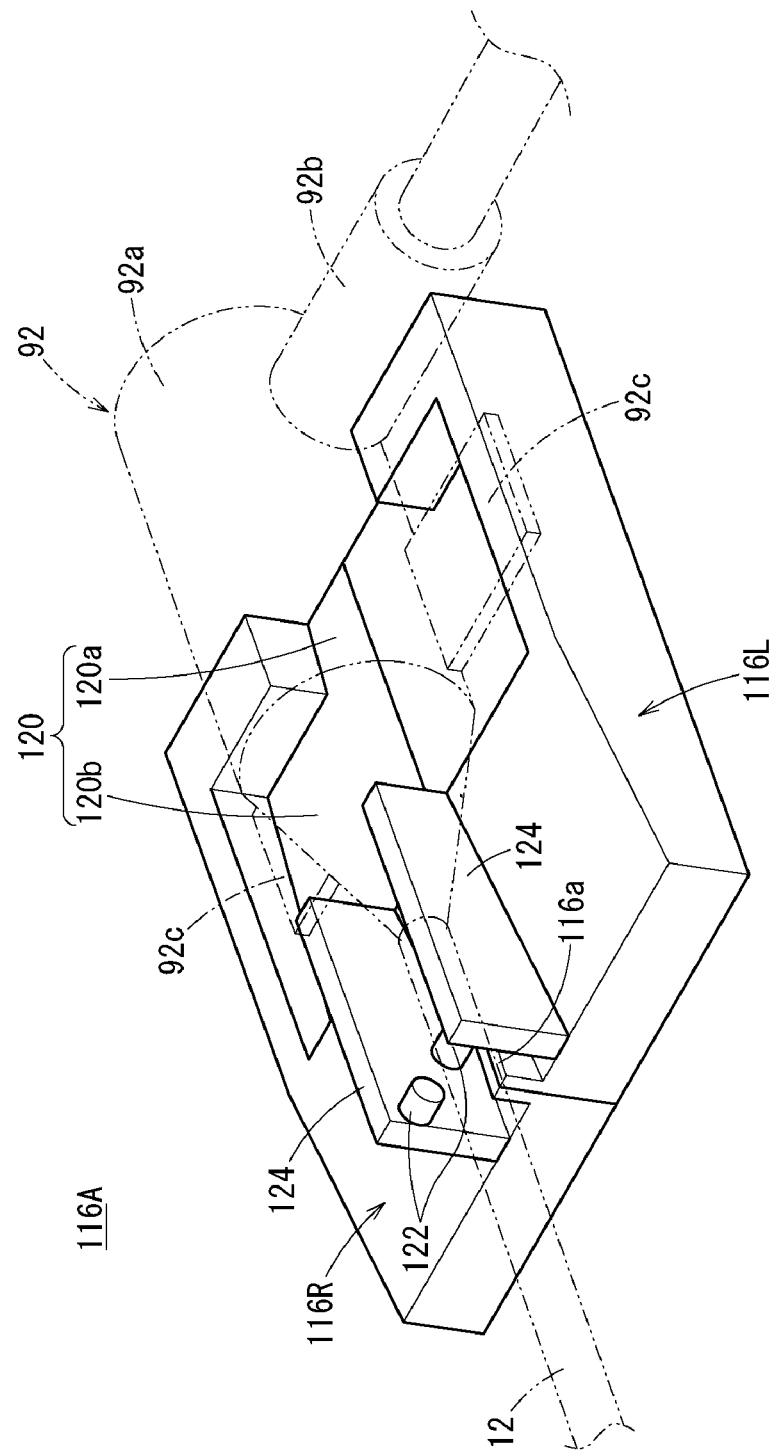
FIG. 28 is a perspective view illustrating a modification of the second deflection suppressing member of the catheter assembly illustrated in FIG. 23.

In the catheter assembly 10K, a second deflection suppressing member 116A illustrated in FIG. 28 may be adopted instead of the above-described second deflection suppressing member 116. The second deflection suppressing member 116A is configured to be split into two left and right members. Specifically, the second deflection suppressing member 116A includes a left member 116L and a right member 116R. A fitting protrusion is provided on one of the left member 116L and the right member 116R, and a fitting hole is provided on the other. In the initial state, the left member 116L and the right member 116R are connected by fitting (temporarily fitting) the fitting protrusion into the fitting hole.

When the catheter 12 is inserted into the patient by a predetermined length, and then, the second deflection suppressing member 116 is removed from the catheter hub 92, the second deflection suppressing member 116 is split in the lateral direction (the left member 116L and the right member 116R are separated from each other in the lateral direction). As a result, it is not necessary to lift the catheter hub 92 at the time of detaching the second deflection suppressing member 116 from the catheter hub 92, kinking of the catheter 12 can be suppressed. Instead of such a lateral split structure (separation structure) by fitting, a configuration in which the left member 116L and the right member 116R are integrally connected via a breakable fragile portion (a thin portion or an intermittent breakable portion) may be adopted.

Figure 29:
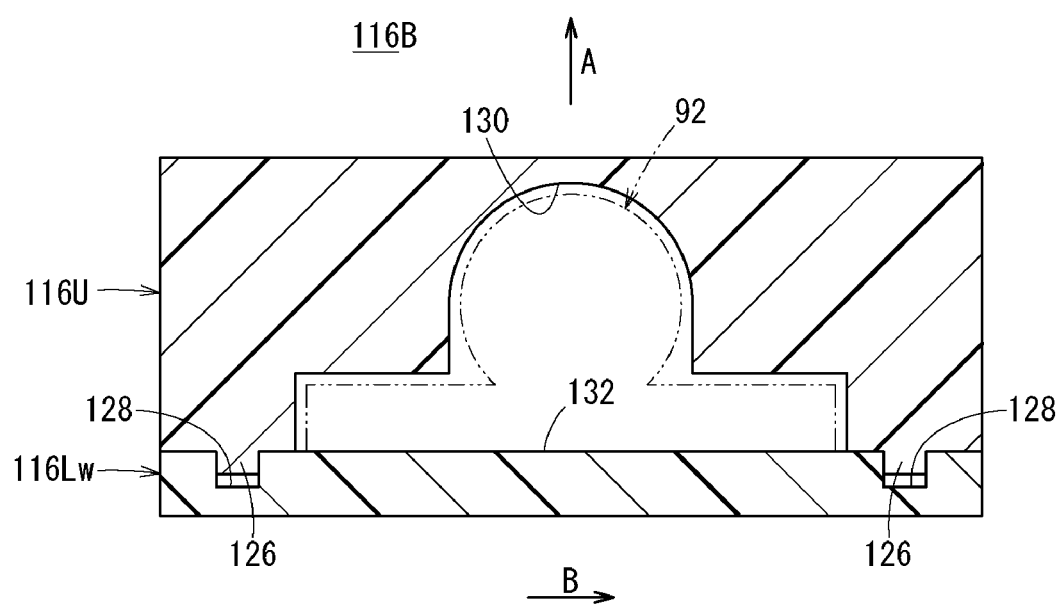
FIG. 29 is a cross-sectional view illustrating another modification of the second deflection suppressing member of the catheter assembly illustrated in FIG. 23.

Alternatively, a second deflection suppressing member 116B that can be split up and down as illustrated in FIG. 29 may be adopted. The second deflection suppressing member 116B includes an upper member 116U and a lower member Lw. The upper member 116U is provided with a fitting protrusion 126 protruding downward, and the lower member Lw is provided with a fitting hole 128 in which the fitting protrusion 126 is fitted. In the initial state, the upper member 116U and the lower member Lw are connected by fitting (temporarily fitting) the fitting protrusion 126 into the fitting hole 128. The upper member 116U is provided with a housing groove 130 following a shape of the catheter hub 92. An upper surface 132 of the lower member Lw is flat.

When the catheter 12 is inserted into the patient by a predetermined length, and then, the second deflection suppressing member 116 is removed from the catheter hub 92, the second deflection suppressing member 116 is split (the upper member 116U and the lower member Lw are separated from each other). Specifically, the upper member 116U is first removed upward (in a direction of an arrow A) in a state where a position of the lower member Lw is fixed. Next, the lower member Lw is moved in the horizontal direction (a direction of an arrow B) to be separated from the catheter hub 92. Because the upper surface 132 of the lower member Lw is flat, the lower member Lw can be removed in the horizontal direction without being caught by the catheter hub 92. As a result, it is not necessary to lift the catheter hub 92 at the time of detaching the second deflection suppressing member 116 from the catheter hub 92, kinking of the catheter 12 can be suppressed.

Alternatively, a modification of the second deflection suppressing member 116 (hereinafter referred to as a "second deflection suppressing member 116M" to be distinguished from the second deflection suppressing member 116) may be configured to be detached upward from the catheter hub 92. The second deflection suppressing member 116M grips the catheter hub 92, and includes a gap that the catheter hub 92 is removed, on the lower side of the catheter hub 92. The wing 92c of the catheter hub 92 has a shape of popping out from the operation portion when viewed from the upper side. When the second deflection suppressing member 116M is removed from the catheter hub 92, the fitting can be removed by moving the second deflection suppressing member 116M upward in a state where the wing 92c is pushed against the patient. As a result, it is not necessary to lift the catheter hub 92 at the time of detaching the second deflection suppressing member 116M from the catheter hub 92, kinking of the catheter 12 can be suppressed.

Twelfth Embodiment

Figure 30:
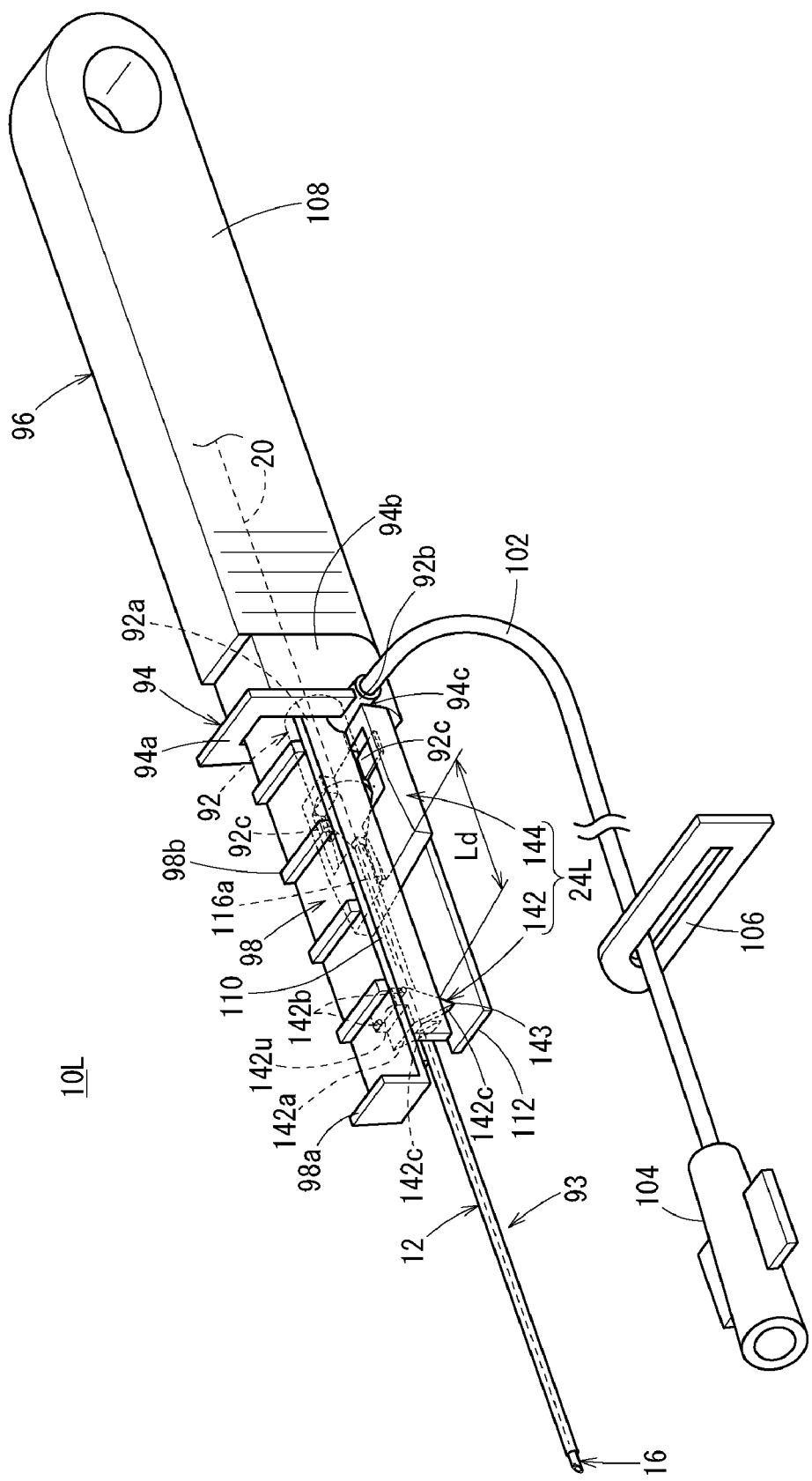
FIG. 30 is a perspective view of a catheter assembly according to a twelfth embodiment of the present invention.

A deflection suppressing mechanism 24L of a catheter assembly 10L according to a twelfth embodiment illustrated in FIG. 30 includes: a first deflection suppressing member 142 that includes an upper deflection suppressing portion 142a and is movably supported by the needle hub 96; and a second deflection suppressing member 144 that includes a lower deflection suppressing portion 144a and holds the catheter hub 92 in a detachable manner in an initial state.

A shaft 142b is provided in an upper portion 142u of the first deflection suppressing member 142. The shaft 142b is pivotally supported by the upper extension portion 110. As a result, the first deflection suppressing member 142 is supported by the upper extension portion 110 so as to be rotatable about an axis that extends in the lateral direction.

The upper deflection suppressing portion 142a includes a sliding contact support portion 143 capable of rubbing against the catheter 12 when the catheter 12 is advanced with respect to the inner needle 16. In the initial state of the catheter assembly 10L, the distal portion of the wire operation member 98 is positioned on the distal side of the upper portion 142u of the first deflection suppressing member 142. Thus, the first deflection suppressing member 142 is restricted from rotating upward by the wire operation member 98.

Figure 31:
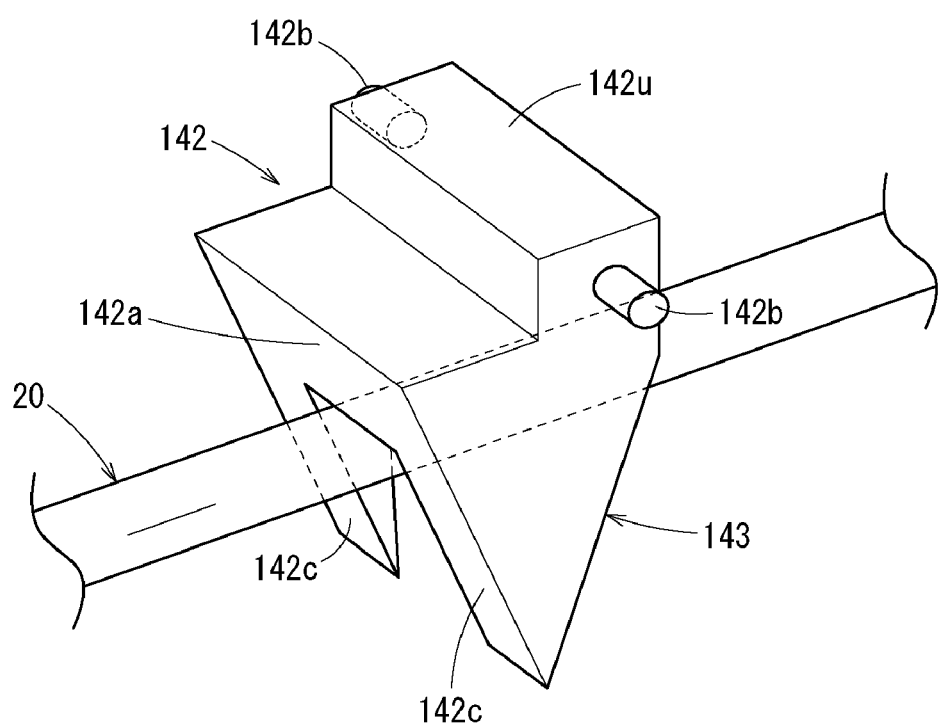
FIG. 31 is a perspective view of a first deflection suppressing member of the catheter assembly illustrated in FIG. 30.

As illustrated in FIG. 31, the sliding contact support portion 143 includes: the upper deflection suppressing portion 142a capable of supporting the catheter 12 from the upper side; and left and right traverse support portions 142c that can support the catheter 12 from the traverse direction. The traverse support portions 142c protrude downward from the left and right ends of the upper deflection suppressing portion 142a. Therefore, the sliding contact support portion 143 is formed in an inverted U shape when viewed from a longitudinal direction of the catheter assembly 10L. In the initial state of the catheter assembly 10L, a slight gap is formed between an outer surface of the catheter 12 and the sliding contact support portion 143.

As illustrated in FIG. 30, the second deflection suppressing member 144 is separably mounted to the catheter hub 92 in the initial state of the catheter assembly 10L. The second deflection suppressing member 144 is a catheter operation member configured to be gripped by the user to advance the catheter 12. The second deflection suppressing member 144 is obtained by eliminating the support plate 124 and the guide protrusion 122 from the second deflection suppressing member 116 illustrated in FIG. 25.

When the second deflection suppressing member 144 is advanced to advance the catheter 12, the first deflection suppressing member 142 rotates upward (and forward) by being pushed by the second deflection suppressing member 144. As a result, the catheter 12 is allowed to be separated from the needle hub 96 in the distal direction. In this case, a distance Ld between the first deflection suppressing member 142 and the second deflection suppressing member 144 along an extending direction of the catheter 12 is set to be relatively large in the initial state of the catheter assembly 10L illustrated in FIG. 30. Thus, the first deflection suppressing member 142 starts to rotate upward after the second deflection suppressing member 144 advances by the distance Ld. Therefore, a deflection suppression function of the first deflection suppressing portion with respect to the inner needle 16 can be maintained until the second deflection suppressing member 144 advances by the distance Ld. The distance Ld is, for example, 5 mm or more, and preferably 20 mm or more.

Thirteenth Embodiment

Figure 32:
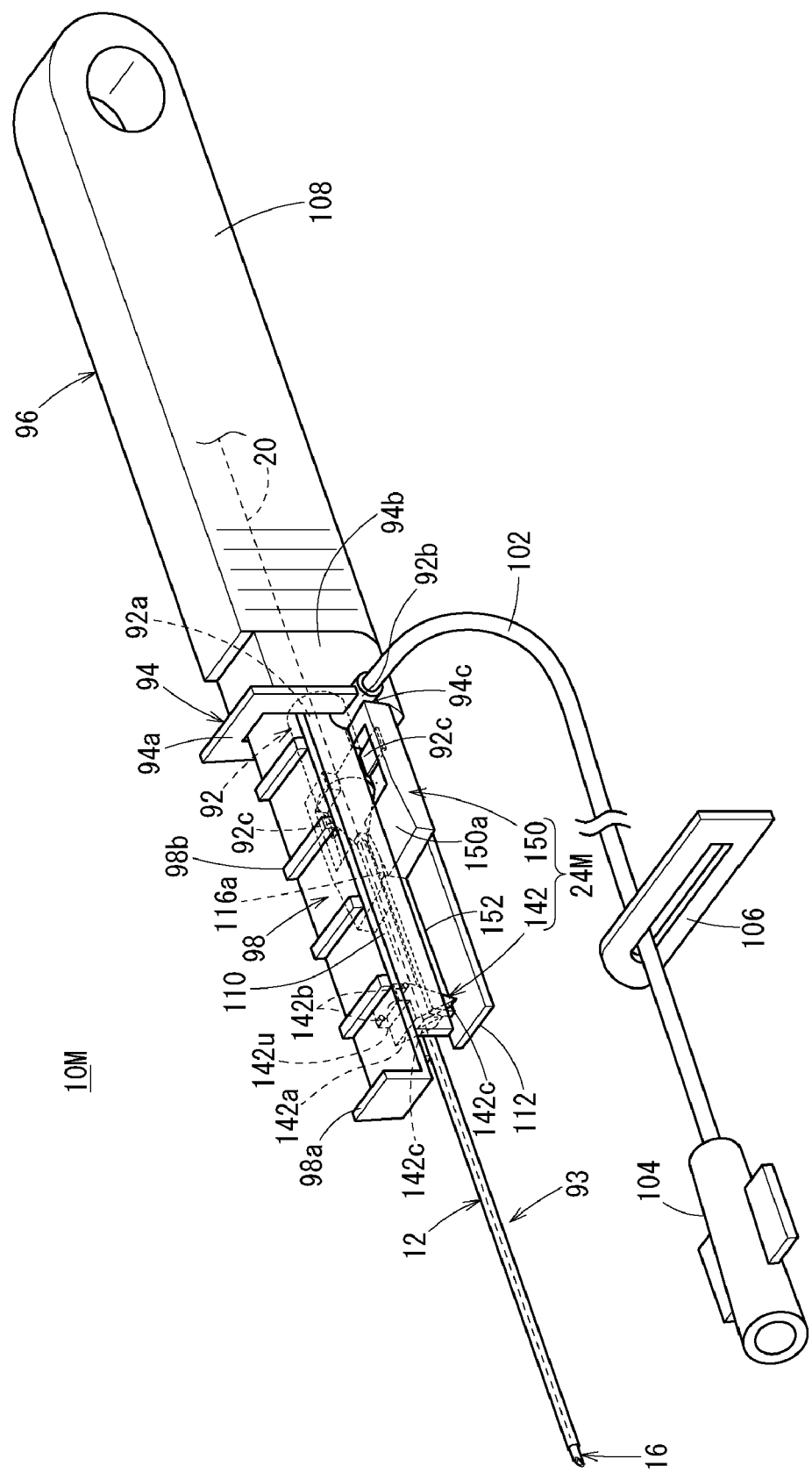
FIG. 32 is a perspective view of a catheter assembly according to a thirteenth embodiment of the present invention.

A deflection suppressing mechanism 24M of a catheter assembly 10M according to a thirteenth embodiment illustrated in FIG. 32 includes: the first deflection suppressing member 142; and a second deflection suppressing member 150 that includes a flexible portion 152 extending around the circumference of the catheter 12. Specifically, the flexible portion 152 is the lower deflection suppressing portion 116a that extends along the catheter 12 on the lower side of the catheter 12 in an initial state of the catheter assembly 10M. The second deflection suppressing member 150 includes a body portion 150a configured similarly to the second deflection suppressing member 144 illustrated in FIG. 30. The flexible portion 152 protrudes from the body portion 150a in the distal direction. The flexible portion 152 is made of an elastic material such as an elastomer.

In the initial state of the catheter assembly 10M, the flexible portion 152 extends up to at least the first deflection suppressing member 142, and the catheter 12 is surrounded by the flexible portion 152 and the first deflection suppressing member 142 over the entire circumference. A slight gap is formed between the flexible portion 152 and the first deflection suppressing member 142, and the catheter 12.

According to the catheter assembly 10M provided with the deflection suppressing mechanism 24M configured as described above, the flexible portion 152 can suppress the deflection of the inner needle 16. Although the flexible portion 152 abuts on the skin at the time of advancing the catheter 12, the flexible portion 152 is bent and does not prevent the advancement of the catheter 12.

The present invention is not limited to the above-described embodiments, and various modifications can be made within a scope not departing from a gist of the present invention.

What is claimed is:

1. A catheter assembly comprising:
   a catheter;
   a catheter hub fixed to a proximal side of the catheter;
   an inner needle inserted through the catheter;
   a needle hub fixed to a proximal portion of the inner needle, the needle hub comprising an upper extension portion and a lower extension portion; and
   a deflection suppressing mechanism that is provided on the needle hub and supports the inner needle via the catheter on a distal side of the catheter hub to suppress deflection of the inner needle; wherein:
   the deflection suppressing mechanism comprises:
     an upper deflection suppressing portion positioned on an upper side of the inner needle, and
     a lower deflection suppressing portion positioned on a lower side of the inner needle;
   the upper deflection suppressing portion is rotatably supported by the upper extension portion of the needle hub;
   the lower deflection suppressing portion comprises a protrusion that is monolithic with the lower extension portion and protrudes from the lower extension portion towards the upper extension portion;
   the upper deflection suppressing portion is movable with respect to the needle hub in order to allow the catheter hub to be detached from the needle hub along with advancement of the catheter with respect to the inner needle; and
   the protrusion includes a support face that supports the catheter and an inclination face adjacent to a proximal side of the support face and inclined in a direction away from the inner needle and in a proximal direction of the inner needle.

2. The catheter assembly according to claim 1, wherein:
the protrusion is an elastic piece that is elastically deformable in the direction away from the inner needle.

3. The catheter assembly according to claim 2, wherein the elastic piece is a leaf spring.

4. The catheter assembly according to claim 2, wherein the elastic piece includes the support face and the inclination face adjacent to a proximal side of the support face and inclined in the direction away from the inner needle and in a proximal direction of the inner needle and the support face extends parallel relative to the catheter.

5. The catheter assembly according to claim 1, further comprising a notch positioned on a lower surface of the upper extension portion, wherein the notch is recessed upward and opposes the lower deflection suppressing portion.

6. The catheter assembly according to claim 5, wherein a distance between the notch and the lower deflection suppressing portion in a direction perpendicular to the length of the catheter is larger than a maximum dimension of the catheter hub in the same direction.

7. The catheter assembly according to claim 1, wherein the support face supports the catheter by contacting a portion of the catheter.

8. A method of using a catheter assembly, the method comprising:
providing the catheter assembly, which comprises:
 a catheter,
 a catheter hub fixed to a proximal side of the catheter,
 an inner needle inserted through the catheter,
 a needle hub fixed to a proximal portion of the inner needle, the needle hub comprising an upper extension portion and a lower extension portion, and
 a deflection suppressing mechanism that is provided on the needle hub and supports the inner needle via the catheter on a distal side of the catheter hub to suppress deflection of the inner needle, wherein:
 the deflection suppressing mechanism comprises:
  an upper deflection suppressing portion positioned on an upper side of the inner needle, and
  a lower deflection suppressing portion positioned on a lower side of the inner needle,
 the upper deflection suppressing portion is rotatably supported by the upper extension portion of the needle hub,
 the lower deflection suppressing portion comprises a protrusion that is monolithic with the lower extension portion and protrudes from the lower extension portion towards the upper extension portion, and
 the protrusion includes a support face that supports the catheter and an inclination face adjacent to a proximal side of the support face and inclined in a direction away from the inner needle and in a proximal direction of the inner needle; and
advancing the catheter with respect to the inner needle, which causes the upper deflection suppressing portion to move with respect to the needle hub and thereby allows the catheter hub to be detached from the needle hub.

9. The method of using a catheter assembly according to claim 8, wherein the catheter assembly further comprises a notch positioned on a lower surface of the upper extension portion, wherein the notch is recessed upward and opposes the lower deflection suppressing portion.

10. The method of using a catheter assembly according to claim 9, wherein a distance between the notch and the lower deflection suppressing portion in a direction perpendicular to the length of the catheter is larger than a maximum dimension of the catheter hub in the same direction.

11. The method of using a catheter assembly according to claim 8, wherein the support face supports the catheter by contacting a portion of the catheter.

\* \* \* \* \*